(12) United States Patent
Bohris

(10) Patent No.: US 7,785,276 B2
(45) Date of Patent: Aug. 31, 2010

(54) SYSTEM AND METHOD FOR A LITHOTRIPTER

(75) Inventor: Christian Bohris, Koailling (DE)

(73) Assignee: Dornier MedTech Systems GmbH, Wessling (DE)

( * ) Notice: Subject to any disclaimer, the term of this patent is extended or adjusted under 35 U.S.C. 154(b) by 1866 days.

(21) Appl. No.: 10/627,578

(22) Filed: Jul. 25, 2003

(65) Prior Publication Data

US 2004/0059319 A1 Mar. 25, 2004

(30) Foreign Application Priority Data

Jul. 26, 2002 (DE) ................. 102 34 144

(51) Int. Cl.
*A61B 17/22* (2006.01)
(52) U.S. Cl. ............... 601/2; 600/407; 600/437; 606/2.5; 606/128; 601/3
(58) Field of Classification Search ........ 600/407, 600/437; 601/2, 3; 606/2.5, 128
See application file for complete search history.

(56) References Cited

U.S. PATENT DOCUMENTS

| | | |
|---|---|---|
| 48,847 A | 7/1865 | Smith |
| 1,750,129 A | 3/1930 | Romine |
| 2,324,702 A | 7/1943 | Hoffman |
| 2,859,726 A | 11/1958 | Bouyoncos |
| 3,056,312 A | 10/1962 | Timpner |
| 3,249,177 A | 5/1966 | Chelminski |
| 3,505,880 A | 4/1970 | Riordan |
| 3,538,919 A | 11/1970 | Meyer |
| 3,555,880 A | 1/1971 | Menius Jr. |
| 3,588,801 A | 6/1971 | Leonard |
| 3,618,696 A | 11/1971 | Hurwitz |
| 3,783,403 A | 1/1974 | Hook |

(Continued)

FOREIGN PATENT DOCUMENTS

DE 1769521 3/1973

(Continued)

OTHER PUBLICATIONS

Wu, "Application of Hydroelastic Waves to the Removal of Small Gallstones," *Transactions of the AMSE*, vol. 103, May 1981.

(Continued)

*Primary Examiner*—Brian Casler
*Assistant Examiner*—Joel Lamprecht
(74) *Attorney, Agent, or Firm*—King & Spalding LLP

(57) ABSTRACT

A system and method for a lithotripter is provided. The system can include a shockwave generator and an ultrasonic transmitting/receiving unit, which are in communication with an evaluating unit. The transmitting/receiving unit can include an ultrasonic transducer that emits ultrasonic pulses and receives ultrasonic waves reflected from a target area of the shockwave generator. The evaluating unit can determine a correlation coefficient of the time correlation between the ultrasonic waves and the ultrasonic pulses and provide a signal related to the coefficient. The method can include emitting ultrasonic pulses from the transducer into a body, receiving the ultrasonic waves reflected from a target object in the body, evaluating the received ultrasonic waves with the evaluating unit to determine the correlation coefficient, and providing a signal related to the correlation coefficient.

148 Claims, 10 Drawing Sheets

U.S. PATENT DOCUMENTS

| | | | |
|---|---|---|---|
| 3,982,223 | A | 9/1976 | Green |
| 3,997,853 | A | 12/1976 | Morris |
| 4,189,026 | A | 2/1980 | Elliot |
| 4,207,874 | A | 6/1980 | Choy |
| 4,272,733 | A | 6/1981 | Walling |
| 4,286,168 | A | 8/1981 | Carr |
| 4,286,455 | A | 9/1981 | Ophir |
| 4,336,809 | A | 6/1982 | Clark |
| 4,336,858 | A | 6/1982 | Loyzim |
| 4,398,790 | A | 8/1983 | Righini |
| 4,493,653 | A | 1/1985 | Robbins |
| 4,494,622 | A | 1/1985 | Thompson |
| 4,546,960 | A | 10/1985 | Abrams |
| 4,549,107 | A | 10/1985 | Kaneko et al. |
| 4,580,559 | A | 4/1986 | L'Esperance |
| 4,639,923 | A | 1/1987 | Tang |
| 4,641,912 | A | 2/1987 | Goldenberg |
| 4,642,611 | A | 2/1987 | Koerner |
| 4,664,111 | A | 5/1987 | Reichenberger |
| 4,669,472 | A | 6/1987 | Eisenmenger |
| 4,672,969 | A | 6/1987 | Dew |
| 4,674,505 | A | 6/1987 | Pauli et al. |
| 4,693,244 | A | 9/1987 | Daikuzono |
| 4,718,421 | A | 1/1988 | Rohwedder et al. |
| 4,721,108 | A | 1/1988 | Heine |
| 4,756,016 | A | 7/1988 | Grady |
| 4,798,196 | A | 1/1989 | Nowacki |
| 4,807,626 | A | 2/1989 | McGirr |
| 4,819,621 | A | 4/1989 | Ueberle |
| 4,829,986 | A | 5/1989 | Eichler |
| 4,962,752 | A | 10/1990 | Reichenberger |
| 4,972,826 | A | 11/1990 | Koehler |
| 5,046,483 | A | 9/1991 | Ogura |
| 5,055,051 | A | 10/1991 | Duncan |
| 5,060,650 | A | 10/1991 | Wurster et al. |
| 5,070,861 | A | 12/1991 | Einars |
| 5,072,722 | A | 12/1991 | Granz |
| 5,072,723 | A | 12/1991 | Vieback |
| 5,072,960 | A | 12/1991 | Sperko |
| 5,090,401 | A | 2/1992 | Schwieker |
| 5,144,953 | A * | 9/1992 | Wurster et al. ............... 600/439 |
| 5,149,030 | A | 9/1992 | Cockrill |
| 5,191,560 | A | 3/1993 | Lobentanzer et al. |
| 5,209,221 | A | 5/1993 | Riedlinger |
| 5,209,222 | A | 5/1993 | Vibach et al. |
| 5,269,306 | A | 12/1993 | Warnking et al. |
| 5,285,772 | A | 2/1994 | Rattner |
| 5,287,856 | A | 2/1994 | Treiber |
| 5,289,856 | A | 3/1994 | Strock et al. |
| 5,301,659 | A | 4/1994 | Brisson |
| 5,358,466 | A | 10/1994 | Aida |
| 5,394,786 | A | 3/1995 | Gettle |
| 5,409,002 | A | 4/1995 | Pell |
| 5,450,848 | A | 9/1995 | Okazaki |
| 5,572,569 | A | 11/1996 | Benoit |
| 5,582,578 | A | 12/1996 | Zhong et al. |
| 5,642,898 | A | 7/1997 | Wise |
| 5,658,239 | A | 8/1997 | Delmenico |
| 5,795,311 | A | 8/1998 | Wess |
| 5,800,365 | A | 9/1998 | Zhong et al. |
| 5,810,748 | A | 9/1998 | Ueberle |
| 5,836,898 | A | 11/1998 | Schwieder |
| 5,864,517 | A | 1/1999 | Hinkey |
| 6,036,611 | A | 3/2000 | Bigo |
| 6,036,661 | A | 3/2000 | Schwarze |
| 6,119,034 | A | 9/2000 | Herrmann |
| 6,135,357 | A | 10/2000 | Herrin |
| 6,276,471 | B1 | 8/2001 | Kratzenberg |
| 6,298,264 | B1 | 10/2001 | Zhong et al. |
| 6,386,560 | B2 | 5/2002 | Calender |
| 6,408,614 | B1 | 6/2002 | Eizenhofer |
| 6,618,206 | B2 | 9/2003 | Tarakci et al. |
| 6,875,176 | B2 * | 4/2005 | Mourad et al. ............... 600/442 |
| 6,915,697 | B2 | 7/2005 | Eizenhofer |
| 6,926,680 | B2 | 8/2005 | Eizenhofer |
| 2001/0048732 | A1 | 12/2001 | Wilson |
| 2002/0095087 | A1 | 7/2002 | Mourad et al. |
| 2002/0125664 | A1 | 9/2002 | Eriksson |
| 2003/0078523 | A1 | 4/2003 | Burkhardt |
| 2005/0010140 | A1 | 1/2005 | Forssmann |
| 2007/0055157 | A1 | 3/2007 | Bohris |
| 2008/0267927 | A1 | 10/2008 | Lutz et al. |

FOREIGN PATENT DOCUMENTS

| | | |
|---|---|---|
| DE | 3723815 | 3/1973 |
| DE | 7532292 U1 | 3/1977 |
| DE | 37 23815 A1 | 6/1988 |
| DE | 3921808 | 6/1988 |
| DE | 3916093 | 11/1990 |
| DE | 3921808 A1 | 1/1991 |
| DE | 4113697 | 1/1991 |
| DE | 9102394.7 | 6/1991 |
| DE | 9102394.7 U1 | 6/1991 |
| DE | 41 13 697 A1 | 11/1992 |
| DE | 41 25 950 C1 | 11/1992 |
| DE | 4125950 | 11/1992 |
| DE | 9414692 | 9/1994 |
| DE | 9414692.6 U1 | 9/1994 |
| DE | 44 43 495 | 6/1996 |
| DE | 4443495 | 6/1996 |
| DE | 4444162 A1 | 7/1996 |
| DE | 4446192 | 7/1996 |
| DE | 19509004 | 10/1996 |
| DE | 19509004 C1 | 10/1996 |
| DE | 29712035 | 10/1997 |
| DE | 29712035 U1 | 10/1997 |
| DE | 19625164 | 1/1998 |
| DE | 19625164 A1 | 1/1998 |
| DE | 19631246 | 2/1998 |
| DE | 19631246 A1 | 2/1998 |
| DE | 19702829 | 7/1998 |
| DE | 19702829 A1 | 7/1998 |
| DE | 19843680 | 9/1998 |
| DE | 19843680 C1 | 9/1998 |
| DE | 197 18 511 C2 | 11/1998 |
| DE | 19718511 | 7/1999 |
| DE | 10111800 | 3/2001 |
| DE | 10111800 A1 | 3/2001 |
| DE | 10206193 | 7/2003 |
| DE | 10206193 C1 | 7/2003 |
| EP | 139823 A1 | 5/1985 |
| EP | 370336 | 8/1988 |
| EP | 369177 | 5/1990 |
| EP | 0 445 322 A | 9/1991 |
| EP | 0 300 315 B1 | 4/1992 |
| EP | 526758 | 2/1993 |
| EP | 0 367 116 B1 | 8/1994 |
| EP | 0 548 048 B1 | 2/1996 |
| EP | 511506 | 10/1996 |
| EP | 715831 | 2/1999 |
| GB | 2799 | 4/1906 |
| JP | 02-215451 | 8/1990 |
| SU | 402070 | 4/1974 |
| WO | WO 86/06269 | 11/1986 |
| WO | WO 88/03782 | 6/1988 |
| WO | WO 96/34567 | 11/1996 |
| WO | WO 00/25125 A1 | 5/2000 |
| WO | WO 00/53263 | 9/2000 |
| WO | WO 01/30281 | 5/2001 |

OTHER PUBLICATIONS

Bachmann, "ESWT und Sonographie der Stütz- und Bewegungsorgane," 1999, pp. 4-19.

Foster, "Flow Velocity Profile via Time-Domain Correlation: Error Analysis and Computer Simulation," *IEEE Transactions on Ultrasonics, Ferroelectrics and Frequency Control*, vol. 37, No. 2, May 1990.

Bonnefous, "Time Domain Formulation of Pulse-Doppler Ultrasound and Blood Velocity Estimation by Cross Correlation," *Ultrasonic Imaging*, 8:73-86, 1986.

Madsen, "Torso Section Phantom for Ultrasonic Imaging," *Medical Physics*, vol. 7, No. 1, Jan./Feb. 1980.

R. F. Paterson et al., "Stone Fragmentation During Shock Wave Lithotripsy is Improved by Slowing the Shock WaveRate: Studies With a New Animal Model," The Journal of Urology® vol. 168, p. 2211-2215, Nov. 2002, Copyright © 2002 by American Urological Association, Inc.®.

H. Wiksell, A.-C. Kinn, "Implications of Cavitation Phenomena for Shot Intervals in Extracorporeal Shock Wave Lithotripsy," British Journal of Urology, 1995, 75, p. 720-723.

P. Hubert, et al., "Influence of Shock Wave Pressure Amplitude and Pulse Repetition Frequency on the Lifespan, Size and Number of Transient Cavities in the Field of Electromagnetic Lithotripter," Phys. Med. Biol. 1998, 43, p. 3113-3128.

R. F. Paterson, et al., "Slowing the Pulse Repetition Frequency in Shock Wave Lithotripsy (SWL) Improves Stone Fragmentation In Vivo," Proceedings of the 17$^{th}$ International Congress on Acoustics, Rome Sep. 2-7, 2001, p. 200-201.

R. F. Paterson, et al., "An in Vivo Test of Shock Wave Rate Effect on Stone Fragmentation in SWL," The Journal of Urology® vol. 165, No. 5, Supplement, Jun. 6, 2001.

Author: Breitung et al. Title: Numerische Simulation von turbelenten Wasserstoff-Verbrennungen bei schweren Kernreaktorunfallen Publ: *Nachrichten* pp. 175-191.

Coleman et al., "A survey of the acoustic output of commercial extracorporeal shock wave lithotripters," Ultrasound in Med. & Biol. 15:213-227, 1989.

Bohris et al., "Hit/miss monitoring of ESWL by spectral Doppler ultrasound,"Ultrasound in Med. & Biol. 29:705-712, 2003.

Zhou et al., "Measurement of high intensity focused ultrasound fields by a fibre optic probe hydrophone," J. Acoust. Soc. Am. 120:676-685, 2006.

\* cited by examiner

SYSTEM AND METHOD FOR A LITHOTRIPTER

CROSS-REFERENCE TO RELATED APPLICATION

This application claims priority to co-pending German Patent Application No. 102 34 144.3, which was filed on Jul. 26, 2002 and is incorporated herein by reference.

FIELD OF THE INVENTION

The invention generally relates to the application of ultrasonic waves to a target object in a body, and more particularly, to a system and method for a lithotripter that can effectively apply such ultrasonic waves.

BACKGROUND OF THE INVENTION

Lithotripters are nowadays widespread as medical devices for destroying concrements, for example kidney stones, in the body of a patient with the help of focused shockwaves. Such lithotripters are commercially offered by the Applicant, for example under the designation "Dornier Lithotripter S" or "Dornier Compact Delta®." In all of these devices, the concrement must be located prior to the beginning of the treatment so that the patient can be positioned with the help of a movable stretcher such that, for example, his kidney stone is within the focus of the shockwaves that are generated with the help of the shockwave generator of the lithotripter. This initial "adjustment," i.e. positioning of the patient, is normally carried out with an imaging locating device, for example an imaging ultrasonic scanner or an X-ray locating device. In addition to the initial locating of the concrement for the first time before the beginning of the ESWL (extracorporeal shockwave lithotripsy) treatment or ESWT (extracorporeal shockwave therapy) treatment, this device also serves to continuously monitor the position of the concrement during the treatment in order to make sure that it has not slipped within the patient's body or traveled to another place or that the patient has not moved on his stretcher, so that the concrement might no longer be in the focus of the shockwaves. For a comprehensive survey of technical and medical aspects of ESWT and of the devices used in lithotripters, reference can be made to the book "ESWT and Ultrasound Imaging of the Musculoskeletal System," Steinkopff-Verlag, Darmstadt, 2001, ISBN 3-7985-1252-3.

As a general rule, the imaging locating device is also used to monitor the success of lithotripsy in the course of the treatment, i.e. fragmentation of the target object. Since a treatment typically takes about 30 minutes, it is usually not feasible to complete the treatment in a continuous manner, because of the excessive radiation dosage of X-rays. Therefore, a treatment is typically conducted during intervals of 3 to 5 minutes. If the target object shifts during the treatment intervals, for example due to a movement of the patient, the patient's body will be loaded by shockwaves, until the next control inspection, without the target object being further fragmented, since it is no longer within the shockwave focus.

In lithotripters in which an ultrasonic scanner is used as the imaging locating device, the scanner may be used continuously for visualizing the target object, but the locating operation is often much more difficult than in radiograms, among other things, because of the image quality, so that even experienced medical personnel will often have difficulties in recognizing the target object or even in evaluating the degree of fragmentation of the object. Moreover, the use of such imaging locating devices not only for the "initial adjustment" of the patient, but also for "hit control" in the course of the treatment has a fundamental drawback. That is, although typically the position of the target object relative to the shockwave focus can thereby be controlled, for example by a purely geometrical quantity, the effect of the shockwaves on the target object itself cannot be detected. Fundamental problems such as an inadequate coupling of the shockwave device to the patient's body, a vignetting of shockwaves (e.g., by ribs), etc., might therefore be detected very late, such as when no effects become visible on the target object in the course of the treatment.

To address the foregoing problems, special ultrasonic methods, particularly ultrasonic Doppler methods, for continuous hit control have been suggested in existing methods, based on the assumption that, when hit, the concrement in the human body will perform a macroscopic movement due to pulse transmission from the shockwave. When the target object is exposed to ultrasonic waves and when the ultrasonic waves reflected on the object are measured, this macroscopic movement will be expressed in a Doppler shift of the frequency of the reflected waves. Lithotripters equipped in this way, where the evaluation of the received ultrasonic waves includes a Doppler analysis, are known, for example, from EP 0 367 116 B1, EP 0 548 048 B1, and DE 44 46 192 A1. These devices have in common that the ultrasonic transducer emits ultrasonic waves into the body and that the ultrasonic waves reflected by the body back to the ultrasonic transducer are sensed, with a Doppler signal unit, which consists of the emitted and received ultrasonic waves, generating and evaluating a Doppler signal, wherein essentially the amount of a frequency shift of the reflected signal relative to the emitted waves is calculated and the hit accuracy is inferred therefrom.

However, the foregoing approach has various drawbacks. For example, it is known that the Doppler signal includes artifacts, especially near its zero point in time (i.e., directly after emission of the shockwave). To prevent the measurement of such artifacts, the lithotripters according to EP 0 367 116 B1 and EP 0 548 048 B1 are, for example, equipped with means for the time synchronization between the shockwave generator and the Doppler signal unit, which makes these devices complicated and expensive. Moreover, in the vicinity of strong scatterers, e.g. a concrement, there may be the so-called mirror artifact in the Doppler spectrum. Due to double reflection, the movement of a scatterer is additionally recorded in the opposite direction. This leads to an additional amount, which corresponds to the useful signal reflected at the zero line. Due to the briefness of the process and the strong artifacts, velocity-time curves, and thus hit information, cannot easily be assigned to the spectra.

Therefore, there is a need in the art to provide a system and method for a lithotripter that determines and displays information about hit control and disintegration control on the basis of received ultrasonic waves, without the need for performing a Doppler analysis, such as that described above, which requires complicated apparatus and is prone to errors.

SUMMARY OF THE INVENTION

The present invention is generally directed to a system and method for a lithotripter. In one aspect, the invention can include a system for a lithotripter, which can include a shockwave generator and an ultrasonic transmitting/receiving unit that communicate with an evaluating unit. The ultrasonic transmitting/receiving unit can include an ultrasonic transducer that can emit ultrasonic pulses and receive ultrasonic waves reflected from a target area of the shockwave generator.

Furthermore, the evaluating unit can determine a correlation coefficient of the time correlation between the ultrasonic waves and the ultrasonic pulses and also provide a signal related to the correlation coefficient.

These and other aspects of the invention will be described further in the detailed description below in connection with the drawings and the claims.

BRIEF DESCRIPTION OF THE DRAWINGS

The accompanying drawings are incorporated into and form a part of the specification for the purpose of explaining the principles of the invention. The drawings are not to be construed as limiting the invention to only the illustrated and described examples of how the invention can be made and used. Further features and advantages will become apparent from the following, and more particular description of the invention as illustrated in the accompanying drawings, wherein.

DETAILED DESCRIPTION OF THE INVENTION

Figure 1:
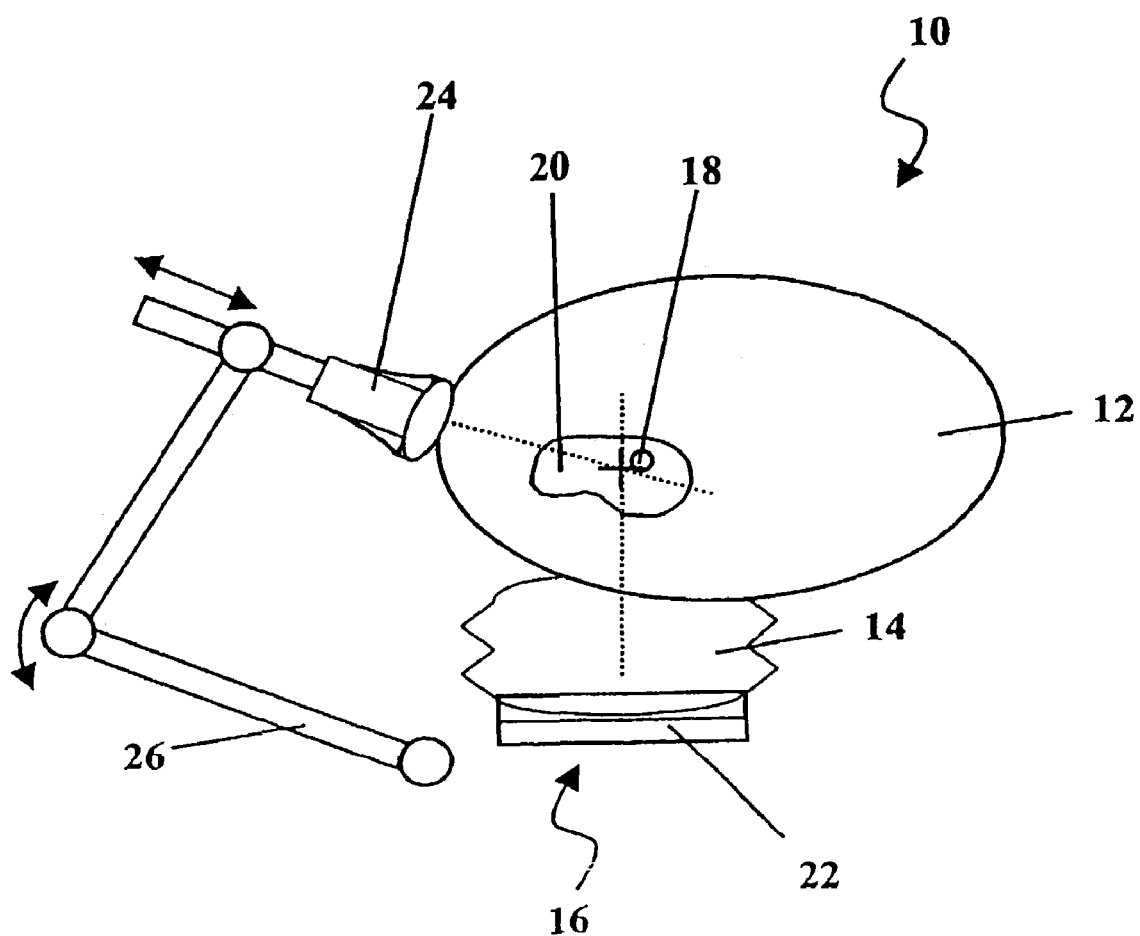
FIG. 1 is a simplified illustration of major components of a lithotripter according to exemplary embodiments of the invention.

The illustrative embodiments of the present invention will be described hereinafter with reference to the drawings, wherein like elements and structures are indicated by like reference numbers. According to exemplary embodiments of the invention, an ultrasonic transducer of a generic lithotripter is designed to emit pulsed ultrasonic waves, and an evaluating unit is designed to determine a coefficient of the time correlation between reflected ultrasonic waves, which are assigned to successively emitted ultrasonic pulses, and to provide an associated correlation coefficient signal. This inventive design of the lithotripter exploits the fact that the more static the reflected system is, for example the body portion in which the target area of the shockwave generator is positioned and in which the ultrasonic waves that are emitted in pulses are reflected, the greater the correlation between successively received "echoes" (i.e., reflected ultrasonic waves).

The following observation can be illustrative in this regard. When the reflecting system, for instance a kidney stone in a kidney of a patient to be treated, has not changed from one emitted ultrasonic pulse to the next one, for example, for the reason that no shockwave has been emitted by the shockwave generator or for the reason that although such a shockwave has been emitted, it has resulted in a "miss" (i.e. the kidney stone has been missed), the first echo (i.e. the reflection of the first emitted ultrasonic pulse) and the second echo (i.e. the reflection of the second emitted ultrasonic pulse) are largely identical. When the time curve of the $i^{th}$ received ultrasonic echo is generally designated as $e_i(t)$ and thus the time curve of a subsequently received ultrasonic echo, which represents the reflection of the $(i+k)^{th}$ emitted pulse, as $e_{i+k}(t)$, the time correlation between the two reflected ultrasonic waves can be defined as:

$$K_{i,k} = \frac{\int_{T_1}^{T_2} e_i(t) e_{i+k}(t)\, dt}{\left(\int_{T_1}^{T_2} e_i^2(t)\, dt\right)^{1/2} \left(\int_{T_1}^{T_2} e_{i+k}^2(t)\, dt\right)^{1/2}} \quad \text{Eq. 1}$$

In this regard, the lower integration limit $T_1$ and the upper integration limit $T_2$ define the time window in which the received echo signals are evaluated. $T_1$ and $T_2$ are here chosen such that the echo originates from the target area of the lithotripter. The mean value of the time window, $(T_1+T_2)/2$, corresponds to the distance between the ultrasonic transducer and the target area of the lithotripter. On the other hand, $(T_2-T_1)/2$ defines the size of the volume used for the evaluation.

In the above formula of Eq. 1, the denominator represents a standardization of the correlation coefficient $K_{i,k}$. In the first considered case of a miss, where the reflecting body area of the patient remains largely static, the ultrasonic echoes $e_i(t)$ and $e_{i+k}(t)$ are identical. Hence, their correlation $K_{i,k}$ is substantially 1. However, due to noise that usually can not be excluded entirely in practice, $e_i(t)$ and $e_{i+k}(t)$ may not be exactly identical, so that $K_{i,k}<1$ is typically applicable in practice.

This situation will change entirely if instead of a miss a hit is achieved with a focused shockwave, for this leads to different effects, each acting on the time curve of the ultrasonic waves received. An interaction mechanism between the shockwave and the concrement leads to a macroscopic movement of the concrement, especially when it has already been fragmented in part or even for the most part. Especially at the beginning of the treatment, when the concrement is still unfragmented to a substantial extent, other effects are prevailing, namely above all the shooting of fragments out of the concrement and the occurrence of cavitation bubbles around the concrement in the case of a successful hit. All of these mechanisms lead to a dynamic movement of areas in the patient's body on which the emitted ultrasonic pulses are reflected and have the overall effect that the stronger the interaction between the shockwave and the concrement and the more the concrement has already been fragmented, the smaller the correlation becomes between ultrasonic echoes corresponding to the reflection of successively emitted ultrasonic pulses. Hence, the correlation coefficient signal provided by the evaluating unit includes the desired information on the strength of the interaction between the emitted shockwave and the target object.

As can be gathered from the terminology used above and regarding the two ultrasonic echoes $e_i(t)$ and $e_{i+k}(t)$, two received ultrasonic waves can be used for determining the time correlation coefficients, which belong to emitted ultrasonic pulses that were not emitted directly one after the other, but are separated by further emitted ultrasonic pulses. However, it is preferable that the evaluating unit be designed to determine the correlation coefficient with the help of reflected ultrasonic waves that are directly assigned to successive emitted ultrasonic pulses. Hence, in the above terminology, this corresponds to the case k=1 and permits the maximal exploitation of the information received by the evaluating unit. In this instance, a look, for example, at the first three ultrasonic pulses that have been emitted after the generation of a shockwave will reveal that the three ultrasonic pulses are reflected in the target area of the shockwave generator, received as echoes 1 to 3 by the ultrasonic transducer, and evaluated in the evaluation unit, which determines the correlation between the first and the second echo, then between the second and the third echo, etc. Following each of the correlation coefficient calculations, an associated correlation coefficient signal is output by the evaluating unit.

As for the further processing of the hit information contained in the correlation coefficient signal, numerous procedures are possible. In one design of the lithotripter according to exemplary embodiments of the invention, the lithotripter further comprises a display device connected to the evaluating unit for displaying the time curve of the correlation coefficient. The correlation coefficients are represented in a coordinate system, where the abscissa is the time since the emission of the last shockwave and the ordinate is the determined correlation coefficient. In the case of a miss, the time curve of the correlation coefficient has a constant value of about 1 over almost the entire period of time between two successive shockwaves. By contrast, in the case of a hit, a "sag" in the time curve of the correlation coefficient is observed, due to the described effects in the target object that influence the reflected ultrasonic echoes. According to general experience, after about 50 to 100 ms, the fragments and the concrement itself will settle down again, and cavitation bubbles will have disappeared again after that period, so that successive ultrasonic echoes will again resemble one another more and more. The correlation coefficient will then relax towards the value 1. Thus, the medical personnel operating the lithotripter can assess whether there is a miss or a hit based on the display, according to exemplary embodiments of the invention.

In addition, or as an alternative, the evaluating unit may be designed to output an error signal if, after the emission of a shockwave, the minimum value of the correlation coefficient does not fall below a predetermined first threshold value. It follows from the above explanation of the impacts of a hit on the correlation coefficient that the time curve thereof shows a sag that becomes more pronounced as the hit becomes better (i.e., the stronger the interaction was between the shockwave and the target object). Accordingly, the sag in the correlation coefficient in the case of a precise hit should be more pronounced. In other words, a miss or a "partial hit" can be recognized due to the fact that in the time-resolved display of the correlation coefficient, which has been described above, the minimum value of the coefficient does not fall below the first threshold value. The output of an error signal in this instance makes it possible to further process the miss information automatically, without an intervention of the medical personnel being needed.

As an another addition or alternative, the evaluating unit may be designed to output an error signal if, after emission of a shockwave, a relaxation time of the correlation coefficient falls short of a predetermined second threshold value, since a hit is also expressed by the feature that the system, consisting of concrement, fragments, and cavitation bubbles, needs a specific minimum time to settle down again according to a minimum relaxation time of the correlation coefficient (i.e., the width of the sag when the correlation coefficient is plotted in time). More specifically, in the course of the whole treatment, the relaxation time can be represented in the form of a continuous display to trace the development of the relaxation time. However, with a successful continuing destruction of the target object, the relaxation time of the correlation coefficient should increase continuously. By contrast, if the relaxation time decreases, this is a strong sign that the concrement has moved out of the shockwave focus, either due to a movement of the concrement (e.g. the movement of a kidney stone within the kidney of the patient) or due to a displacement of the patient himself. If desired, the screen may also be used as a display device on which the images supplied by the imaging locating device are shown.

The relaxation time can be determined in different ways. For instance, the evaluation unit can be designed to determine the relaxation time by adapting a Gauss curve to the time curve of the correlation coefficient. Depending on the curve shape occurring in practice, it may also be expedient to adapt a function of the form $1-A^{(-t/T_R)}$ to the time curve of the correlation coefficient, wherein $T_R$ is the relaxation time to be determined by adaptation. Likewise, it is possible in some embodiments of the invention to define the relaxation time $T_R$ via threshold values, i.e. as the difference of those points of time at which the time curve of the correlation coefficient falls below a specific threshold value for the first time or, in the relaxation phase, will then rise again above the threshold value. Such curve adaptations ("fitting") and threshold value analyses can nowadays be carried out by numerous data processing systems rapidly and reliably, so that a real time control of the shockwave therapy is possible with the help of the evaluating unit.

In an advantageous development of some exemplary embodiments of the invention, a lithotripter may comprise an alarm device connected to the evaluating unit, which is fed with the error signal, and in this case, the alarm device can be expediently designed to output an optical and/or acoustic alarm. Thus, the alarm device can, for example, emit a warning sound or a warning light as soon as it follows from the supplied error signal that the minimum value of the correlation coefficient does not fall below the first threshold value or that the relaxation time thereof falls below the second threshold value, which indicates a miss in each case. In addition, or as an alternative, the alarm may be triggered when the relaxation times measured show a negative trend, since in the case of a disintegration, a rising relaxation time must be assumed.

Alternatively, or in addition, the shockwave generator may be connected to the evaluating unit and designed to stop or continue the generation of shockwaves as a function of the error signal. An automatic switching off of the shockwave generator is thereby accomplished, i.e. when the target object is apparently no longer within the shockwave focus. Hence, independently of the attention or of the reaction time of the medical personnel operating the lithotripter, an unnecessary loading of the patient's body by shockwave misses can be avoided.

The above-mentioned threshold values, which, when exceeded or fallen below, have the effect that the evaluating unit outputs error signals, can be preset in the evaluating unit as a rule and both the technical data of the shockwave generator (for example, its performance) and typical data of the patient can be taken into account in this process. Expediently, however, the evaluating unit can comprise adjusting means for adjusting the first and/or second threshold value. In this instance, the threshold values can also be set individually at the beginning of the treatment, for example, in consideration of the arising signal noise. The threshold values can also be determined automatically on the basis of the signal itself, since among the signals acquired prior to the beginning of the shockwave therapy, it is possible to determine an ideal curve of the correlation coefficient and also of background noise.

In a development of the lithotripter according to exemplary embodiments of the invention, the evaluating unit may be designed to smooth the variation of the values of the correlation coefficients, for example, by averaging. The number of the correlation coefficient values over which the averaging operation is performed is preferably chosen to be variable. It is thereby prevented that, for example, an individual "outlier," which may be caused, for example, by a numerical artifact during calculation of a correlation coefficient, leads to the output of the error signal by the evaluating unit. Likewise, a synchronization between the ultrasonic transducer and the shockwave source may be carried out to prevent electromagnetic interference caused by the operation of the shockwave source and originating from one of the echoes received at that very moment from having a strongly interfering effect, which might lead to an outlier in the correlation coefficient.

Furthermore, the evaluating unit may also be designed to average the minimum value and/or the relaxation time of the correlation coefficients over several shockwaves. The following geometrical circumstances of a typical lithotripsy treatment are considered in this regard. The shockwave focus has a typical extension of about 4 mm. A typical concrement, e.g. a kidney stone, has dimensions between 5 and 20 mm at the beginning of the treatment, and it may be moved back and forth by the mere breathing of the patient at an amplitude of about 30 mm. Under these conditions, a few shockwaves would be bound to miss the concrement, because the emission of shockwaves is typically carried out without regard to the respective breathing state of the patient. The minimum values of the correlation coefficient that are directly measured after such shockwaves are particularly large, as explained above, and in an extreme case, the correlation coefficient has the constant value of 1. Accordingly, the relaxation times measured directly after such shockwaves are particularly short so that, irrespective of which of the two parameters forms the basis for the output of an error signal, the alarm device would always be operated and/or the shockwave generator would be switched off, although there is no maladjustment of the patient. Instead, it is preferred that the next shockwaves would already hit the concrement again because they are emitted in another breathing state of the patient. In the averaging of the minimum values or the relaxation time over several shockwaves, an averaging operation over, for example, five shockwaves may first be carried out in a first adjustment of the evaluating unit. But, for a further enhancement of the treatment efficiency, it is recommended that the number of the shockwaves over which the averaging operation is carried out should be set individually at the beginning of the treatment of the patient in dependence upon his typical breathing behavior, the size of the concrement to be fragmented, etc. As an alternative to a smoothing or averaging operation, other types of signal filtering operations are also possible, such as a median filtering.

In those versions of generic lithotripters that perform Doppler analyses, it has been found out in clinical experiments that numerous ultrasound measurements are definitely dependent on individual patients. Therefore, the evaluating unit may be designed in an expedient development of the lithotripter according to exemplary embodiments of the invention to standardize the minimum value and/or the relaxation time of the correlation coefficient to the reference minimum value or the reference relaxation time of a reference correlation coefficient curve. The reference correlation coefficient curve can be expediently recorded at the beginning of the treatment, when the patient has been adjusted in the above-described way in the lithotripter such that, as can be monitored with the help of the imaging locating device, a kidney stone, for instance, is located at least substantially in the shockwave focus. In the above-mentioned display of the process (i.e., the continuous plotting, for example, of relaxation times) in the course of the shockwave treatment, there will typically, thus, be no plotting of absolute relaxation times of the correlation coefficient, but standardized relaxation times will be plotted.

In the procedure that has so far been described, the correlation coefficient is calculated according to the above formula of Eq. 1. It has the effect that a fragmentation of the target object effects a sagging in the time curve of the correlation coefficient, which will relax according to a typical relaxation time towards the value of 1, when the system consisting of target object, fragments, and cavitation bubbles settles down again after the hit. However, the formula of Eq. 1 will also lead to a decrease in the correlation coefficient if the concrement has, for example, shifted slightly due to the breathing movement of the patient between the emission of the $i^{th}$ ultrasonic pulse and the $(i+k)^{th}$ ultrasonic pulse. The evaluating unit operating according to the formula of Eq. 1 would then already calculate a decrease in the correlation coefficient, because, due to the shifting of the target object, the time curve $e_{i+k}(t)$ of the $(i+k)^{th}$ received ultrasonic echo is shifted on the time abscissa in comparison with the curve $e_i(t)$ of the $i^{th}$ ultrasonic echo. This is due to the fact that, for example, in the case of a slight movement of the concrement away from the ultrasonic transducer, the $(i+k)^{th}$ emitted ultrasonic wave has to cover a somewhat longer distance than the $i^{th}$ wave before being reflected, and as a consequence, the $(i+k)^{th}$ echo must travel the same additional distance.

To eliminate such effects on the calculated correlation coefficient, it may be intended in some exemplary embodiments of the lithotripter that the evaluating unit is designed to determine a cross correlation function in time between reflected ultrasonic waves and to determine the maximum value of the cross correlation function in time as a correlation coefficient. In this instance the evaluating unit calculates the correlation coefficient substantially according to the following formula:

$$K_{i,k} = \max\nolimits_{\Delta t} \left( \int_{T_1}^{T_2} e_i(t) e_{i+k}(t - \Delta t) dt \right) \qquad \text{Eq. 2}$$

The expression of Eq. 2 in brackets represents the cross correlation function with the variable $\Delta t$.

Hence, in exemplary embodiments of the invention related to Eq. 2, the evaluating unit shifts the measured variation of the $(i+k)^{th}$ ultrasonic echo along the time abscissa by an amount $\Delta t$ each time and it is only then that it will form the time integral, similar to the formula of Eq. 1. The correlation coefficients calculated in this way for numerous values of $\Delta t$ are temporarily stored, and their maximum is finally determined as the correlation coefficient $K_{i,k}$ that is looked for. This algorithm is known as a cross correlation method and is used in the medical field, for example in the determination of blood flow velocity profiles, wherein substantially that value of $\Delta t$ is looked for that yields the maximum of K. Reference can be made to the publication, "Flow Velocity Profile via Time-Domain Correlation: Error Analysis and Computer Simulation" by Steven G. Foster, Paul M. Embree, William D. O'Brien Jr., IEEE Transactions on Ultrasonics, Ferroelectrics and Frequency Control, Vol. 37, no. 2, May 1990, page 164, and to the publication, "Time Domain Formulation of Pulse-Doppler Ultrasound and Blood Velocity Estimation by Cross Correlation" by 0. Bonnefous and P. Pesque, Ultrasonic Imaging 8, 1986, pages 73-85. As to possible medical information that might be contained in Δt, the temporary storing of the measuring parameters may also be implemented.

Expediently, in the ultrasonic transducer of exemplary embodiments of the invention, the ultrasonic transmitting/receiving unit is mounted on an adjustable holder. The ultrasonic transducer can then be adjusted independently of other parts of the lithotripter for optimizing the ultrasonic signals received and can be fixed in the optimum position. It is thereby particularly ensured that the ultrasonic transducer is directed to the shockwave focus. As an alternative to the so-called isocentric scanner guidance, a so-called inline transducer may also be used (i.e. an ultrasonic transducer which is integrated into the shockwave source).

Generally, the following should be considered. With the adjustable holder, a line is just defined along which, in a pulse (PW) method, an emitted ultrasonic pulse propagates in the tissue and echoes are generated. In the case of an isocentric construction, it will then be ensured that the shockwave focus, i.e. the target area, is positioned along the line. With known means, such as a displacement sensor, it is possible to determine the distance of the transducer relative to the focus. On the basis of the known propagation time of ultrasonic pulses in the tissue, it is possible, in turn, to define a time window on the basis of the distance (namely, the time window ($T_1$, $T_2$) according to the formula of Eq. 1), which cuts out that part of the echo that was generated in the target area.

In some exemplary embodiments of the lithotripter of the invention, the ultrasonic transmitting/receiving unit may be designed as part of an imaging ultrasonic scanner (e.g., a duplex scanner). In this instance, the ultrasonic transducer and parts of the electronic system of the ultrasonic transmitting/receiving unit can simultaneously be used for ultrasonic imaging and for measuring the ultrasonic echo pulses.

Alternatively, the ultrasonic transducer may be designed as an inexpensive pin probe, which makes it flexibly usable when employed with the above-mentioned holder, for example, in order to ensure that it is always directed onto the shockwave focus. Such a design is particularly recommended when the lithotripter, in accordance with embodiments of the invention, further comprises an X-ray locating device. In this instance, the imaging is carried out at the beginning of the positioning of the patient and in the detail control, which takes place about every three to five minutes with the help of the imaging X-ray locating device, while the continuous hit control is carried out with the help of the ultrasonic transducer designed as the pin probe. Also in this instance, the correlation coefficient may be displayed on the display device that is also used for displaying the X-ray images.

FIG. 1 is a schematic view showing major mechanical components of the lithotripter 10 according exemplary embodiments of the invention. A patient 12 can be positioned on an adjustable stretcher (not shown) such that a coupling cushion 14 of a shockwave generator 16 can be pressed at the desired place onto the body of the patient 12 to emit shockwaves towards a concrement 18 to be fragmented in the body of the patient 12. In the case schematically illustrated in FIG. 1, the concrement 18 is a kidney stone in the kidney 20 of the patient 12. The patient 12 can be "adjusted" (i.e. positioned) with the help of the adjustable stretcher such that the focus of the shockwaves, that are generated by a shockwave source 22 of the shockwave generator 16 and transmitted with the help of the coupling cushion 14 into the body of the patient 12, is located in kidney stone 18, the focus being outlined in FIG. 1 by a cross-hair. The adjustment is typically carried out with the help of an imaging locating device, e.g. an X-ray device or an ultrasonic scanner. The components of the lithotripter 10 and an exemplary procedure of the positioning of a patient prior to the beginning of the treatment are generally known and, therefore, not be explained in further detail.

Additionally, the lithotripter 10 according to exemplary embodiments of the invention can comprise an ultrasonic transducer 24 mounted on an adjustable holder 26. In the exemplary illustration of FIG. 1, the holder 26 is typically designed in the form of a hinged arm and permits an exact positioning of the ultrasonic transducer 25 at a desired place of the body of the patient 12 in such a manner that the ultrasonic transducer 24 can be directed onto the shockwave focus, as illustrated in FIG. 1 by dotted lines. This arrangement is called an isocentric scanner guidance.

Figure 2:
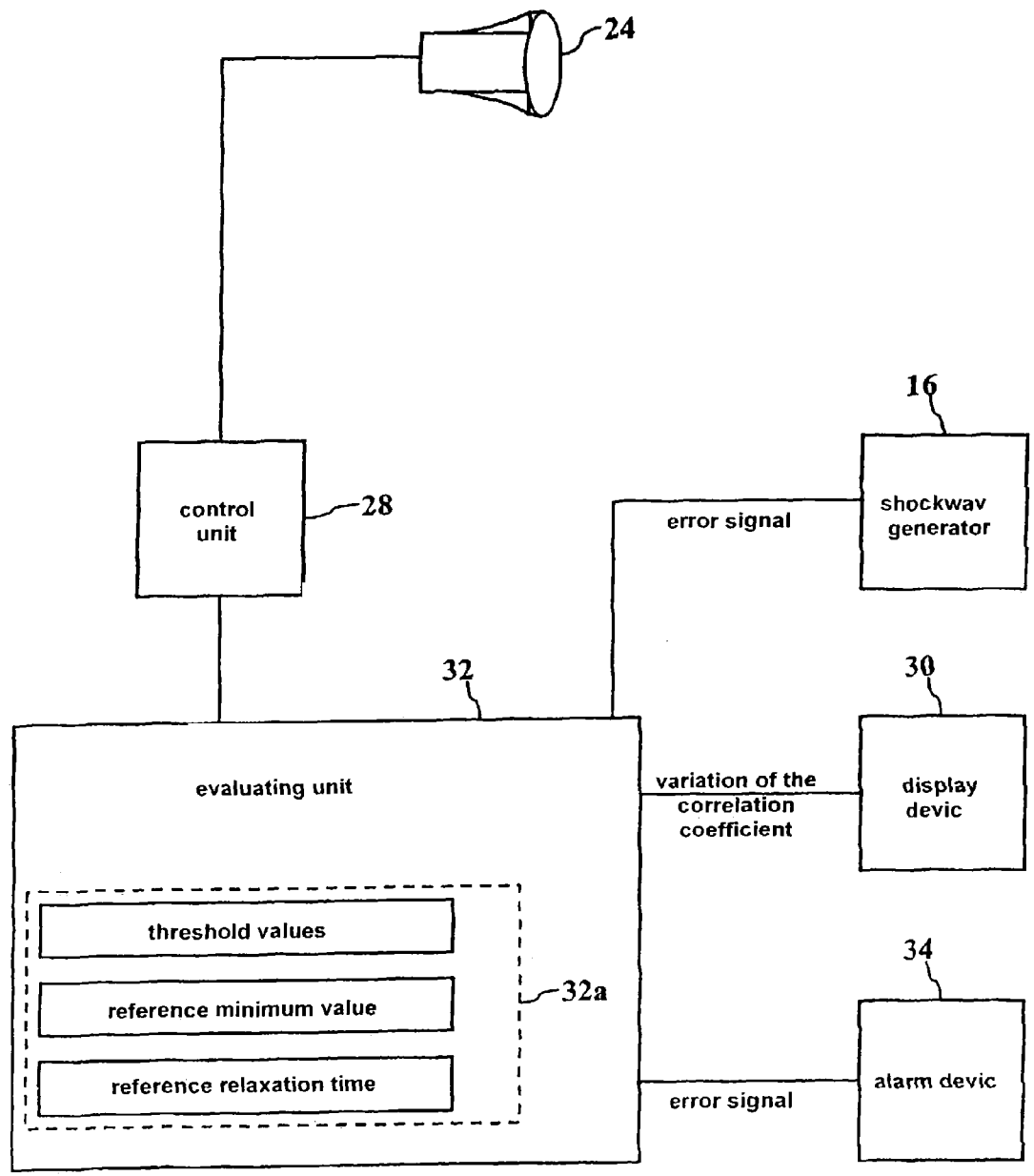
FIG. 2 is a schematic view of the evaluating unit and its connections in the lithotripter according to exemplary embodiments of the invention.

The ultrasonic transducer 24 transmits ultrasonic waves towards the shockwave focus in pulses, e.g. pulsed wave (PW), and further receives ultrasonic waves that have been reflected in the body of the patient 12, particularly from the area of the shockwave focus. As illustrated in FIG. 2, the received ultrasonic signals are supplied by the ultrasonic transducer 24 to a control unit 28, which controls the operation of the ultrasonic transducer 24 as part of a transmitting/receiving unit, e.g. the piezoelectric elements contained in it, and senses the reflected ultrasonic signals measured by the ultrasonic transducer 24. The control unit 28 also passes the signals onto downstream electronic units. For instance, the control unit 28 could pass on the received ultrasonic signals to an image processing module (not shown), with the help of which, ultrasonic images of the kidney stone 18 can be displayed on a display device 30.

Irrespective of this feature, the control unit 28 in the lithotripter 10, according to exemplary embodiments of the invention, supplies the received ultrasonic signals to an evaluating unit 32, which is designed such that it determines a time correlation coefficient between reflected ultrasonic waves that are assigned to successively emitted ultrasonic pulses. These features will be explained with reference to FIGS. 3 and 4.

Figure 3:
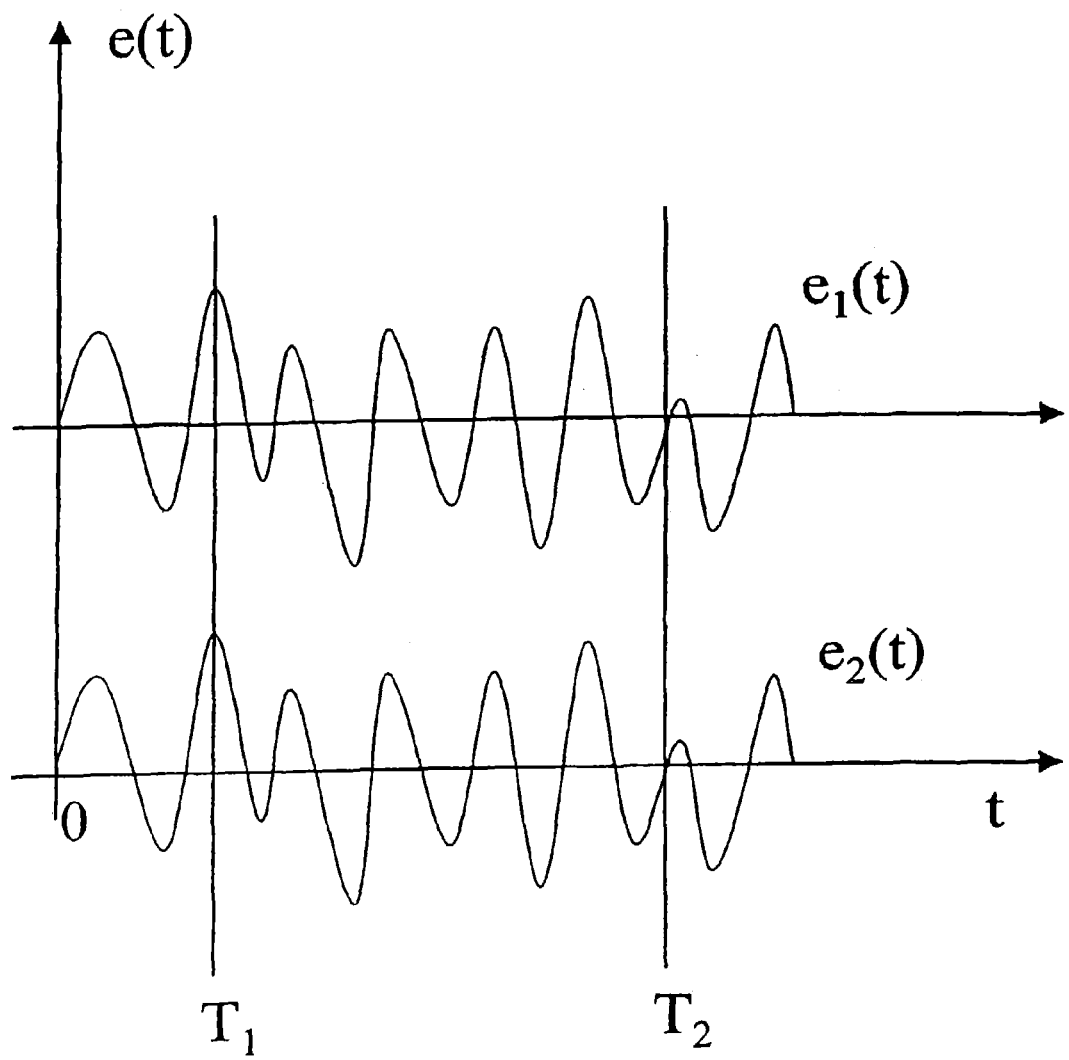
FIG. 3 shows an example of two successively received ultrasonic wave echoes that were reflected on a static system following the miss of a shockwave.

The ultrasonic transducer 24 emits ultrasonic pulses at a frequency of typically about 1 kHz, which are reflected in the body of the patient 12, namely, due to the previous adjustment of the ultrasonic transducer 24 with the help of the adjustable holder 26 in a target area of the shockwave generator 16. Since the shockwave generator 16 emits about one shockwave per second, this means that about 1000 ultrasonic pulses are emitted into the body of the patient 12 between two shockwaves and that, as a consequence, about 1000 ultrasonic echoes are also received. These received ultrasonic echoes are in general designated as $e_1$, $e_2$ ... $e_{1000}$. FIG. 3 shows the time-resolved characteristic of two immediately successively received ultrasonic echoes, $e_1(t)$ and $e_2(t)$, in a purely exemplary way, and it should be noted that the evaluating unit 32 resets an internal time counter to zero again upon each emission of an ultrasonic pulse.

In FIG. 3, the case is shown where the target area of the shockwave generator 16 in which the emitted ultrasonic waves are reflected is entirely static, for example, on account of the fact that shockwaves are not at all emitted at the moment, or also because of the fact that emitted shockwaves miss the concrement 18. Hence, the concrement 18 remains immobile; there are neither shifts nor fragmentations of the concrement 18, and there are also no cavitation bubbles in the direct vicinity of the concrement 18. Accordingly, the time characteristics of the two ultrasonic echoes $e_1(t)$ and $e_2(t)$ under consideration are almost identical, so that the correlation calculated according to the above-indicated formula of Eq. 1 by integrating the product $e_1(t) \cdot e_2(t)$ over the time window of $T_1$ to $T_2$ is at a maximum and will assume approximately the value of 1 upon a suitable scaling according to the above formula of Eq. 1.

Figure 4:
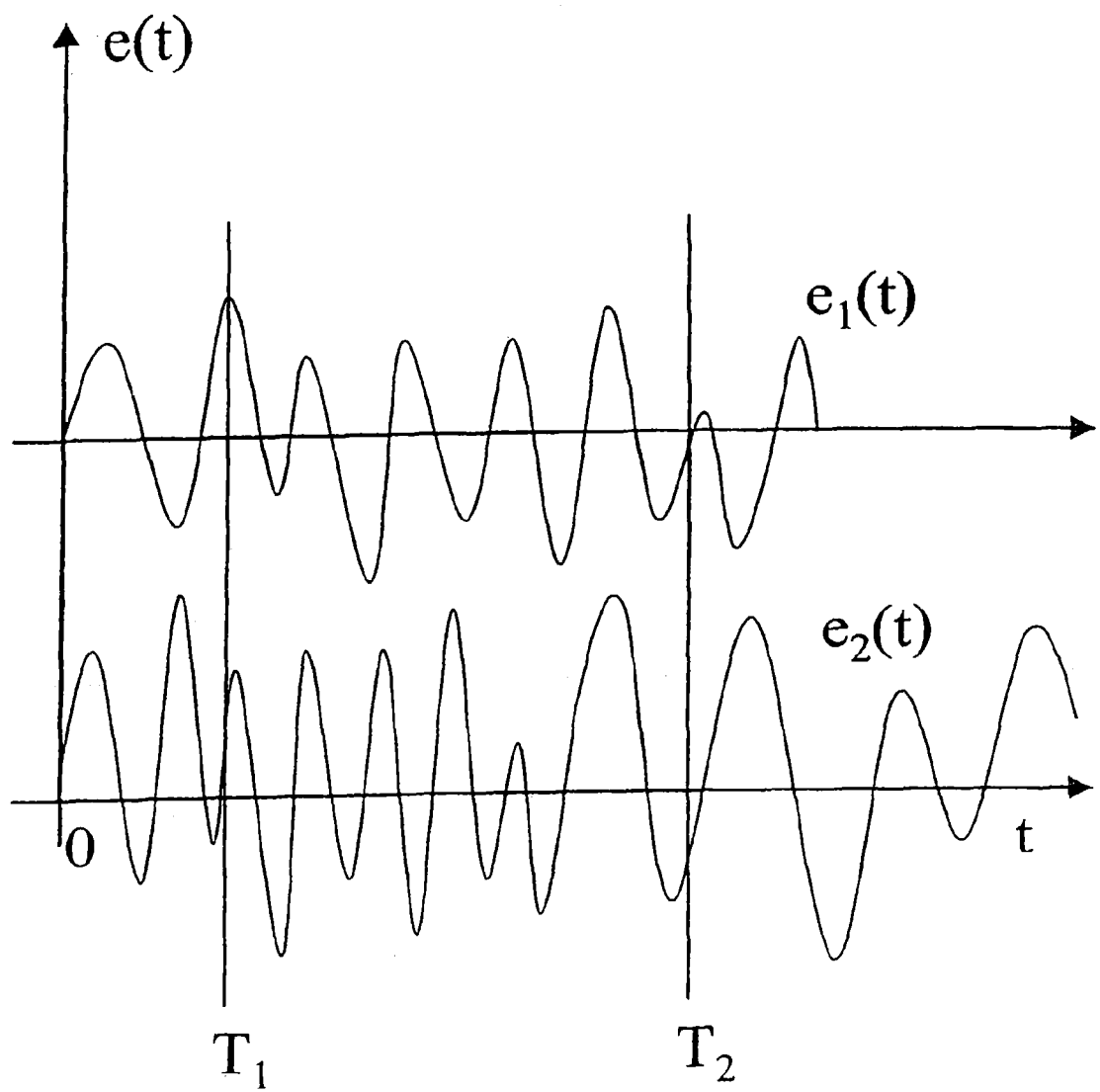
FIG. 4 shows an example of two successively received ultrasonic shockwave echoes that were reflected on a system in motion following a hit of the shockwave.

FIG. 4 shows a case in which the ultrasonic echo $e_1$ was right away reflected on the same immobile target area, but the concrement 18 was hit by a shockwave immediately thereafter. When the concrement 18 is positioned in the shockwave focus, so that a hit is achieved upon emission of the shockwave, small fragments are knocked out of the concrement 18 and the concrement 18 is simultaneously restructured internally. Furthermore, in the direct vicinity of the concrement 18, increased cavitation is observed in the fluid inherent to the body of patient 12. All of these processes have the effect that the ultrasonic waves emitted by the ultrasonic transducer 24 towards the concrement 18 are increasingly reflected on objects that, relative to the transducer 24, are not only at another position than the one immediately before this, upon reflection of echo $e_1$, but are also in movement relative to transducer 24.

The mere fact that specific reflecting areas, for example, the concrement 18 itself, have moved based on the directly preceding reflection (e.g., away from transducer 24), leads to changed signal propagation times and thus to a shift in curve $e_2(t)$ relative to curve $e_1(t)$. Moreover, the fact that, due to the hit, specific reflecting areas are now no longer static, but in motion, effects changes in the signal curve in the reflected echo $e_2$ (i.e. complex changes in the signal-time function). Additionally, the increased cavitation caused upon a hit in the direct vicinity of the concrement 18 can lead to an uncontrolled movement of reflecting objects (e.g., density variations or gas bubbles in the body fluid of patient 12), which can also lead to changes in the signal curve.

A macroscopic movement of the concrement 18, which might particularly arise in cases where it is already fragmented at least in part, leads to both a change in signal propagation times and a complex change in the signal-time function when the concrement 18 performs a kind of oscillatory movement due to elastic forces of the surrounding tissue. Therefore, a look at FIG. 4 will reveal that the correlation coefficient calculated according to the above formula of Eq. 1 will be smaller between the time curves $e_1(t)$ and $e_2(t)$ than in the example shown in FIG. 3, referring to largely identical echoes that are reflected on a static system. The evaluating unit 32 continuously calculates the correlation coefficients between $e_1$ and $e_2$, between $e_2$ and $e_3$, between $e_3$ and $e_4$, etc., which become continuously smaller due to the above-described mechanisms in the case of a shockwave hit on the concrement 18. According to experience, the fragments and the concrement 18 itself will settle down again after such a hit, typically after 50 to 100 ms. The cavitation bubbles will also have disappeared again after the end of this period, so that successive echoes $e_i$, $e_{i+1}$ start to resemble one another again more and more, and the correlation coefficient calculated by the evaluating unit 32 thus relaxes again towards its maximum value 1 (i.e. rises).

Figure 5:
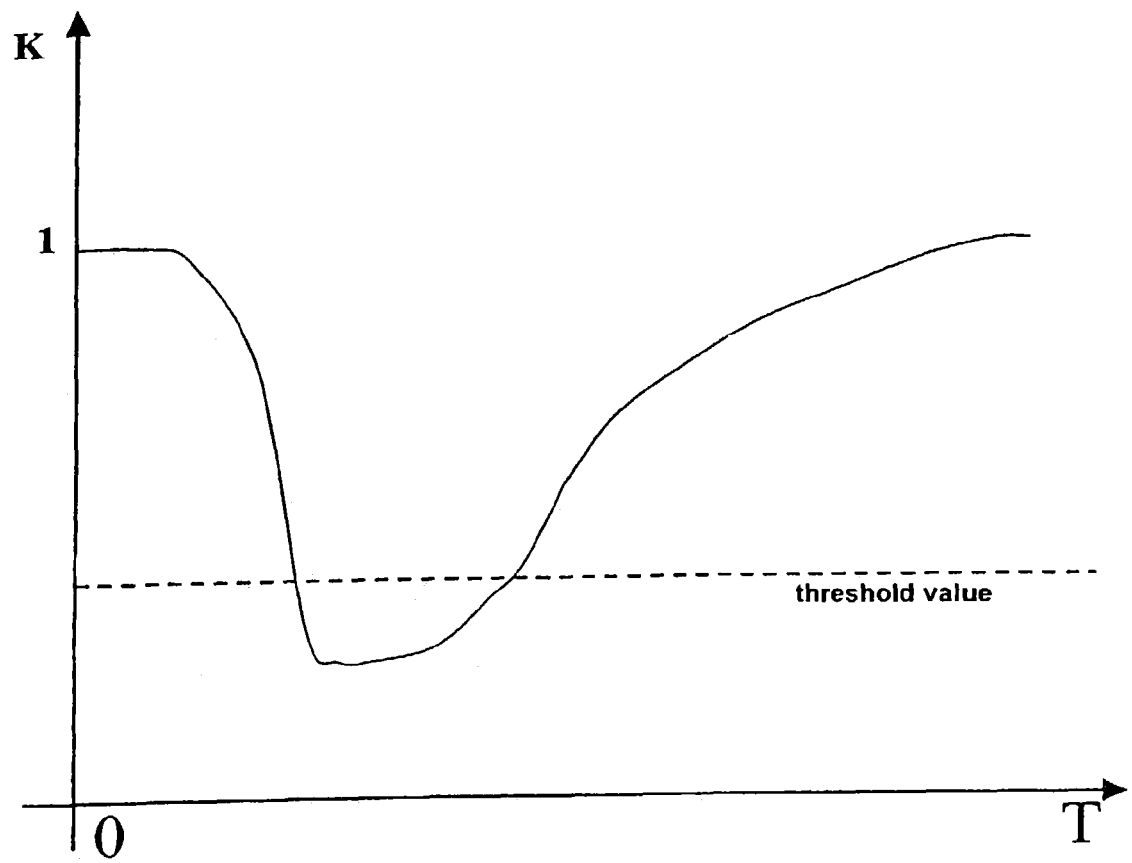
FIG. 5 shows a schematic example of the variation of the correlation coefficient with time upon a hit of a shockwave.

As has already been explained above, it is preferably assumed that the characteristic of the correlation coefficient is described by a function of the form $1-A^{(-t/T_R)}$. However, in response to the individual situation the curve characteristic may also be similar to a Gauss curve, at least sectionwise. The characteristic of the correlation coefficient K to be thus expected, which is a function of time, is shown in FIG. 5. As described above, correlation coefficient values of about K=1 can be seen at the beginning and end of the illustration, and a pronounced "sag" in the K curve can be seen in the middle of the illustration of FIG. 5. This sag can be described by two characteristic parameters that can be used independently and also in combination for identifying a hit of the shockwave.

On the one hand, a direct hit has the effect that the value of K falls below a predetermined threshold value, which is depicted in FIG. 5 by a horizontal broken line. On the other hand, it could generally be detected in shockwave treatments that the relaxation time $T_R$ (i.e., the time passing until the system of concrement 18 and of knocked-out fragments comes to rest again) is a measure of a hit. Hence, the width of the K curve according to the relaxation time $T_R$ can also serve as a measure of a hit. Therefore, the evaluating unit 32 is designed to generate an error signal whenever the minimum of the correlation coefficient does not fall short of a predetermined first threshold value and/or whenever the relaxation time $T_R$ of the correlation coefficient falls below a predetermined second threshold value. It can be assumed here that misses or partial hits of the shockwave past the concrement 18 lead at best to very small sags in the K curve whereas the relaxation time $T_R$ becomes longer as the concrement 18 is more precisely hit by the shockwave.

As illustrated in FIG. 2, the error signal generated by the evaluating unit 32 is supplied to the shockwave generator 16 and an alarm device 34. The shockwave generator 16 can thus be stopped automatically, if necessary, in case of misses. An unnecessary load on the body of the patient 12 by the shockwave misses is thereby avoided in a particularly reliable and efficient way without any intervention of the medical personnel being needed. The alarm device 34 can trigger an acoustic and/or optical alarm if an entered error signal indicates a miss. In such a case the medical personnel can manually switch off the shockwave generator 16 or take other measures, for example, newly adjusting the patient 12.

Figure 6:
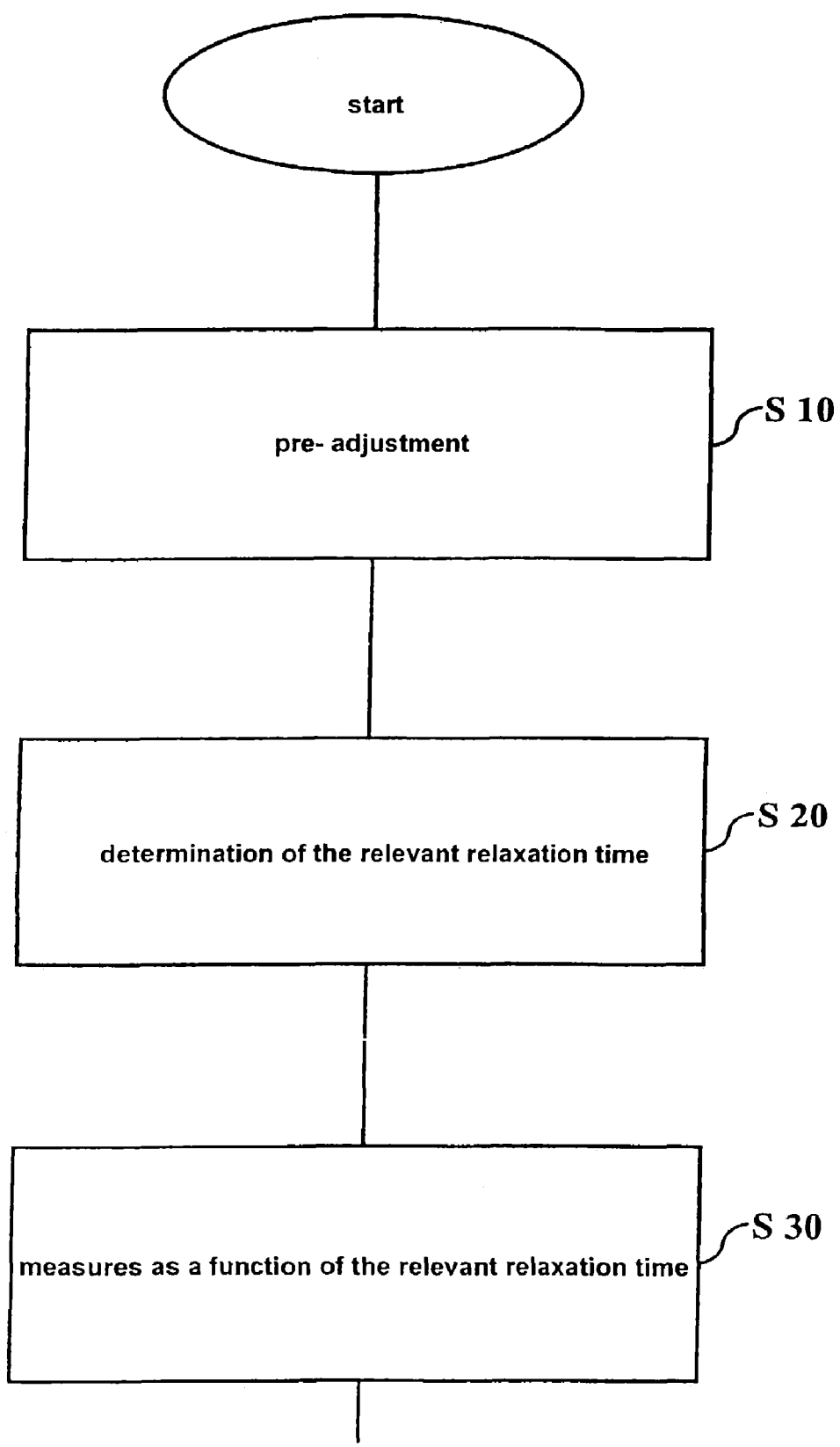
FIG. 6 shows a schematic flow diagram for illustrating the major sections of the method according to exemplary embodiments of the invention.

As schematically shown in FIG. 6, a method in accordance with exemplary embodiments of the invention includes three sections after the lithotripter 10 has been started, namely a first section S10 with steps for pre-adjusting the lithotripter before the therapy proper, a subsequent section S20 in which, during therapy, the relevant relaxation time $T_R$ is determined in various steps of the method, and a further section S30 in which the corresponding measures are taken in several method steps as a function of the relevant relaxation time $T_R$ determined in section S20. It should be noted that for the sake of simplicity, only the sensed relaxation time $T_R$ is used in the following as a basis for the hit control, but it is of course also possible that the minimum of the correlation coefficient K according to FIG. 5 or a combination of both parameters is used by the evaluating unit 32 for generating an error signal.

Figure 7:
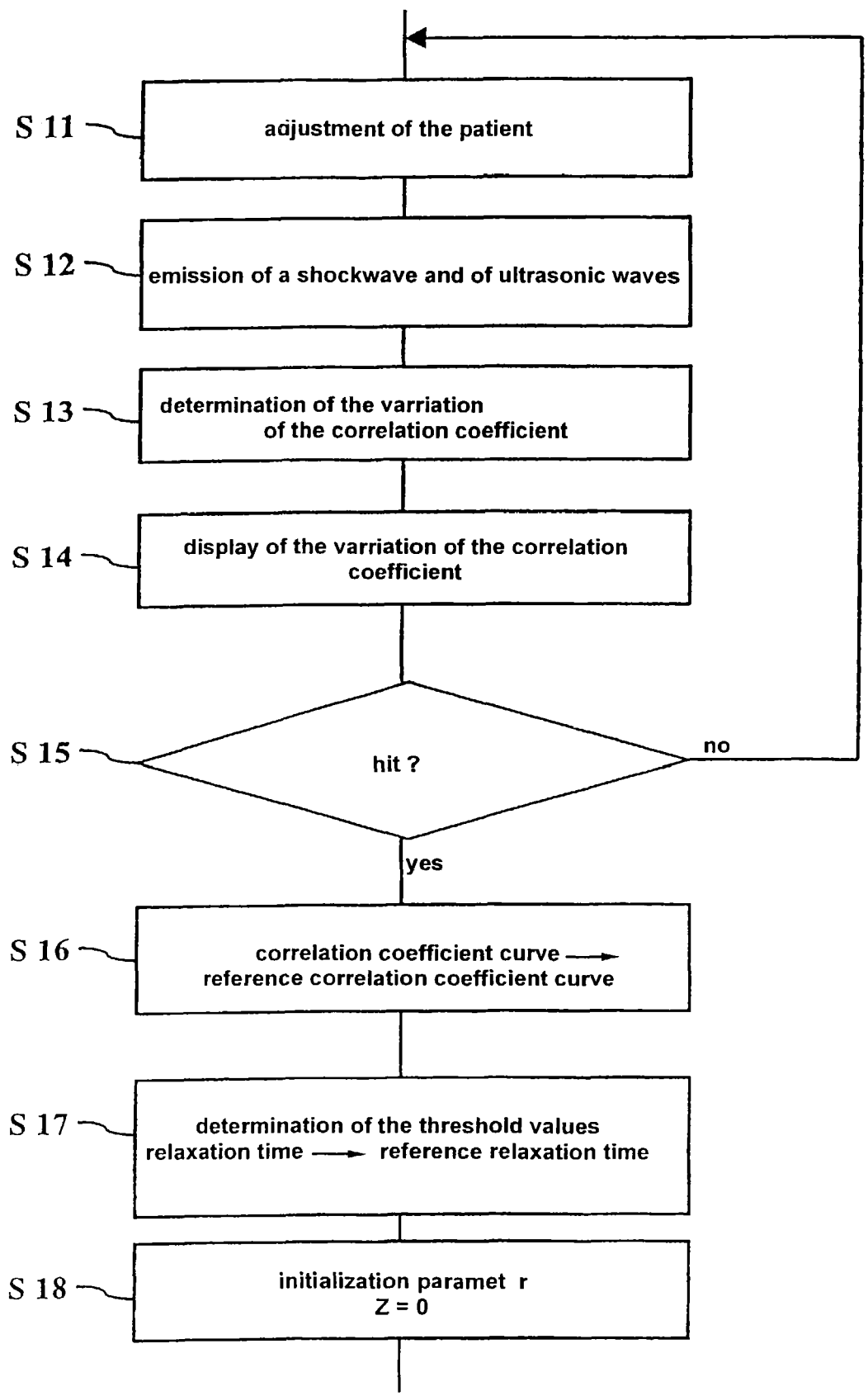
FIG. 7 shows a schematic flow diagram for illustrating method steps of the first main section illustrated in FIG. 6.

Exemplary steps of the first section S10 can be explained with reference to FIG. 7. First, the patient is adjusted in step S11 with the help of the adjustable stretcher of the lithotripter 10. At the end of this adjustment, which is monitored by an imaging locating device, the patient 12 is positioned such that the concrement 18 is within the shockwave focus. Subsequently, the emission of ultrasonic waves by the ultrasonic transducer 24 and the emission of a shockwave for the first time with the help of shockwave generator 16 are started in step S12.

Subsequently, in step S13, the evaluating unit 32 determines the characteristic of the correlation coefficient with the help of the reflected ultrasonic echo in the above-described way, the correlation coefficient being then displayed in step S14 on the display device 30 according to FIG. 5. A fit curve, which has been adapted (i.e., "fitted") by the evaluating unit 32 to the sag in the K curve can already be displayed on the display device 30 in this step. This characteristic of the correlation coefficient is inspected in step S15 by the medical personnel as to whether it indicates a hit or a miss.

Typically, this first emission of a shockwave in step S12 yields a hit, because after step S11, the concrement 18 is positioned within the shockwave focus, and because prior to the emission of this one "test shockwave," one can ask the patient 12 to stop breathing for a short period of time, so that a miss due to a breathing movement of the concrement 18 is not imminent. In this inspection of correlation coefficient characteristics as to whether there is a hit or a miss, it is, among other things, important that the respective signal noise is determined, such as variations that arise upon reflection of the ultrasonic wave on a resting patient 12 without the emission of shockwaves. If a hit is not detected in step S15, step S11 is resumed. By contrast, if a hit is detected, the measured correlation coefficient curve is stored in step S16 as a reference correlation coefficient curve in memory 32a of the evaluating unit 32.

With the help of the reference correlation coefficient curve in memory 32a, the above-discussed threshold values are then defined in step S17. In case these are exceeded or not reached, this will have the effect that the evaluating unit 32 supplies an error signal. Furthermore, in step S17, the relaxation time $T_R$, which is determined in the reference correlation coefficient curve, is stored in memory 32a as a reference relaxation time. An initialization (i.e. a resetting of a count parameter Z), whose significance will become clear in the following from FIG. 8, is then performed in step S18.

Figure 8:
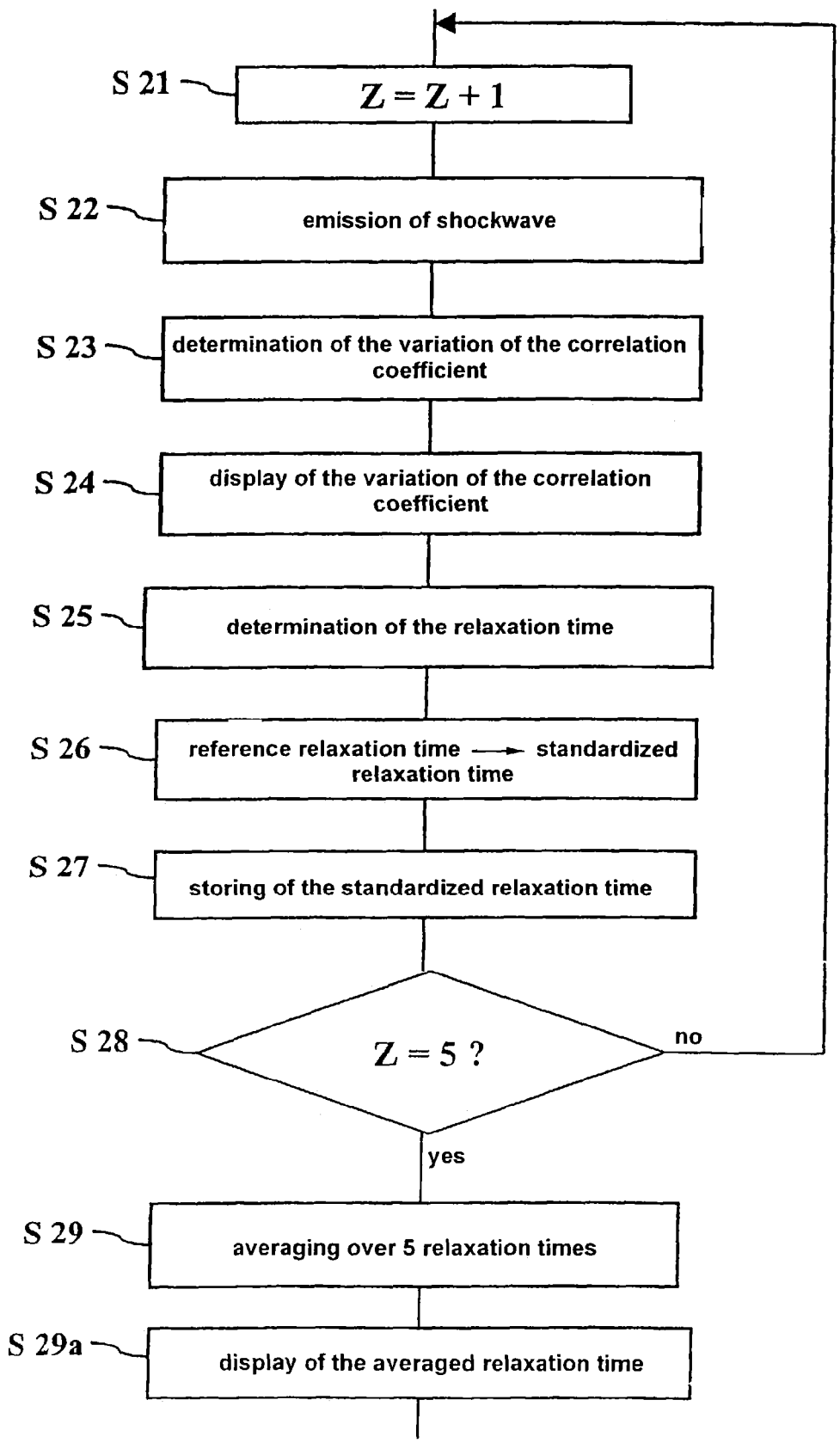
FIG. 8 shows a schematic flow diagram for illustrating method steps of the second main section according to FIG. 6.

FIG. 8 shows exemplary steps within the second section S20 according to FIG. 6 which may serve to determine the relevant relaxation time $T_R$. First, the count parameter Z is incremented in step S21 (e.g., increased by 1). A shockwave is subsequently emitted in step S22 by the shockwave generator 26. The characteristic of the correlation coefficient is determined in step S23 and subsequently displayed in step S24 on the display device 30, just like an optionally adapted fit curve.

In the subsequent step S25, the relaxation time $T_R$ of the actual correlation coefficient curve is determined with the help of the fitted Gauss curve (other fit curves or evaluation methods are possible, such as those fundamentally known in the field of data evaluation). In step S26, the relaxation time $T_R$ is converted by means of a division by the reference relaxation time determined in step S17, according to FIG. 7, into a standardized relaxation time $T_R$, which will then be stored in step S27 in the evaluating unit 42, for example, in the memory 32a or in a separate memory for receiving measured values.

It is then checked, in step S28, whether the count parameter Z has reached a predetermined value, namely the value Z=5 in the example shown in FIG. 8. If this is not the case, the program executed in the evaluating unit 32 returns to step S21, in which the count parameter Z is incremented and a further correlation coefficient characteristic is then measured. However, when the examination in step S28 reveals that the count parameter Z has reached the predetermined value, for example Z=5 (which means that the relaxation times of 5 preceding correlation coefficient characteristics are temporarily stored in the evaluating unit 32), the program continues and goes to a step S29 in which an averaging operation over the five temporarily stored relaxation times is carried out. The mean value of the relaxation times of the last five correlation coefficient curves that are calculated in step S29 can also be stored temporarily in the evaluating unit 32 in one of the memories.

In step S29a, the mean value that is the last calculated one is added to a continuous display, which continuously displays the relaxation times measured in the course of the whole treatment to trace the development of the relaxation times. Expediently, the continuous display can be shown on the display device 30, but this may also be a separate screen, etc. An example of such a continuous display is shown in FIG. 10 and shall be explained further below.

Figure 9:
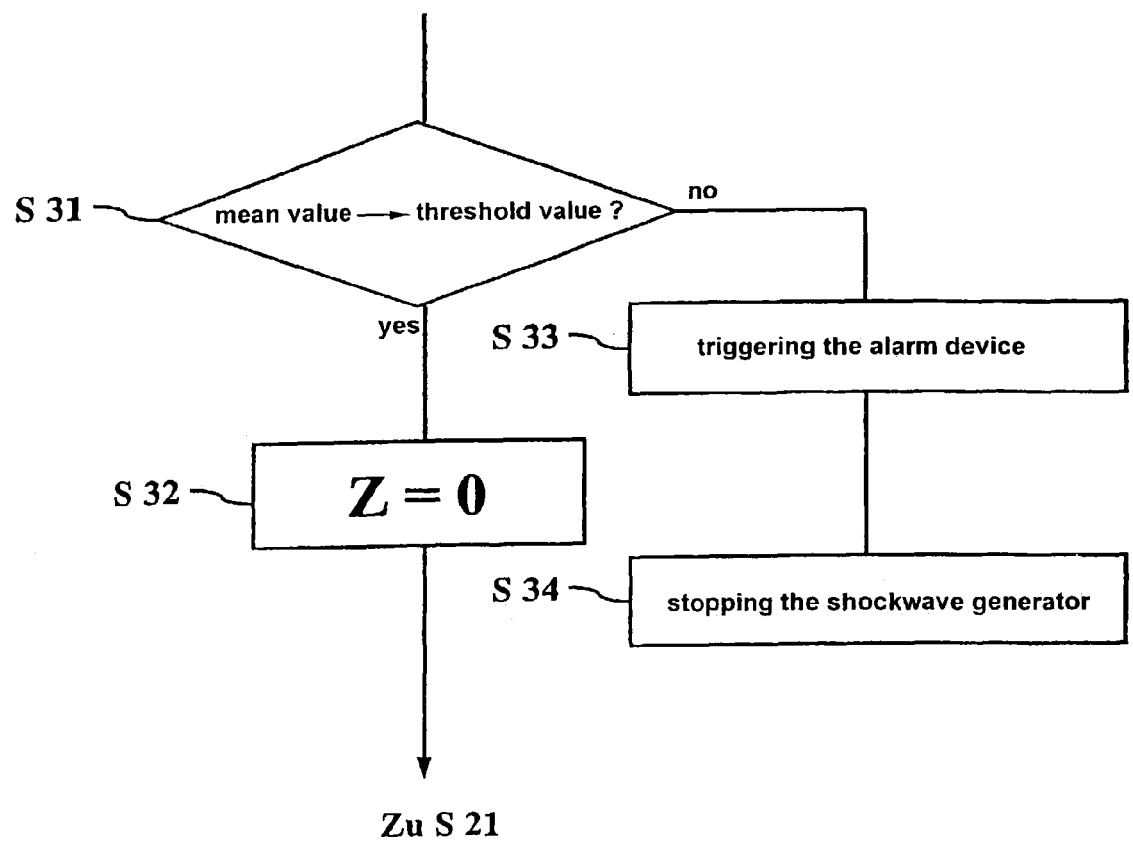
FIG. 9 shows a schematic flow diagram for illustrating method steps of the third main section according to FIG. 6.

FIG. 9 shows exemplary steps of the third section S30 according to FIG. 6 and the measures that can be taken within the scope of the method of the invention during a lithotripsy treatment with the lithotripter 10 of the invention as a function of the mean value calculated in step S29. In a step S31, it is checked through the program executed in the evaluating unit 32 whether the mean value calculated in step S29 is larger than a predetermined threshold value. As explained above, large relaxation time values indicate a hit, whereas small relaxation time values are typical of misses. Consequently, a positive result of the examination in step S31 means that the concrement 18 is apparently still within the shockwave focus and hits are thus made. As a result in this case, the program executed in evaluating unit 32 goes back to S21 via step S31, in which the count parameter Z is reset to 0 (i.e. the program starts a new measurement of five standardized relaxation times with a subsequent averaging operation according to FIG. 8). However, when the examination in step S31 reveals a negative result, for example, the averaged relaxation time $T_R$ of the last five correlation coefficient characteristics is too short, (which indicates possible misses), the evaluating unit 32 outputs an error signal and the program branches off to a step S33 in which the alarm device 34 is triggered, and subsequently to a step S34 in which the shockwave generator 16 is stopped to avoid unnecessary load on the body of the patient 12 by misses.

Figure 10:
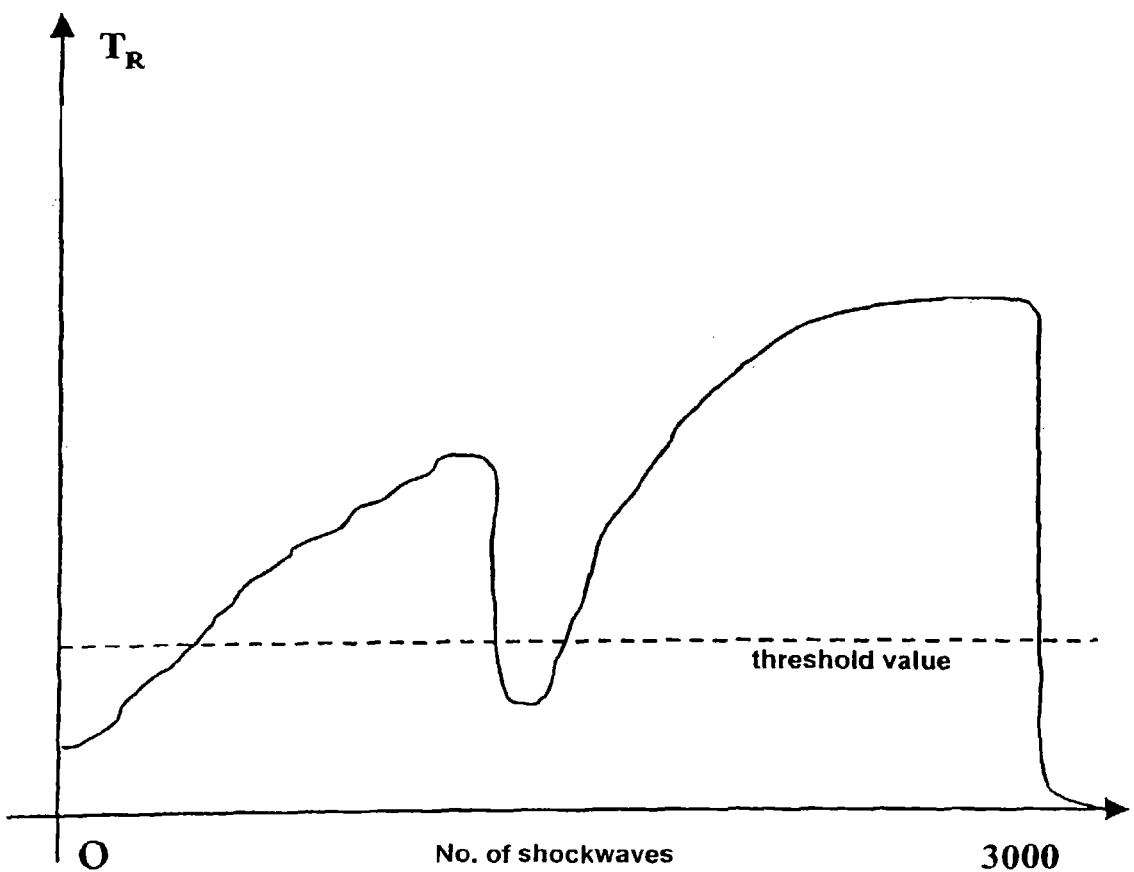
FIG. 10 shows a schematic example of a relaxation-time variation control during a shockwave therapy.

FIG. 10 is a schematic illustration showing an exemplary variation control display on the display device 30 during a shockwave therapy. FIG. 10 reveals a coordinate system, the abscissa of which indicates the number of emitted shockwaves, and the ordinate of which indicates the absolute or standardized relaxation time $T_R$ determined subsequent to the respective shockwave. As depicted, from the start of the shockwave therapy until shortly before the end thereof, there is a characteristic corresponding to a slow rise in relaxation time $T_R$. Individual "sags" in this characteristic curve indicate misses that have been caused by a movement of the patient 12 or of the concrement 18 within the patient 12 and that have been corrected immediately by newly positioning the patient 12. In FIG. 9, a horizontal broken line represents the amount of the threshold value which will trigger the alarm device 34 if not reached. As can be seen, the local sag has led approximately in the middle of the characteristic curve to a falling short of the threshold value and thus to an alarm.

It is noted that FIGS. 6-10 show exemplary steps of methods in accordance with exemplary embodiments of the invention and that numerous additional preceding, succeeding, and/or intermediate steps are possible, including those that are basically known in the field of lithotripsy methods. It also noted that, as mentioned above, the minimum value of the correlation coefficient (e.g., in FIG. 5) can also be used instead of or in addition to the relaxation time $T_R$ to detect a miss. Since in the illustration of FIG. 5 hits lead to deep and simultaneously broad sags, the area contained in the "sag" of the K curve can also be determined numerically and used as a measure of a hit or a miss. Furthermore, it is noted that the number Z=5, as indicated in step S28, is a mere exemplary value. To be more specific, this number can also be entered individually by medical personnel within the pre-adjustments according to section S10 in FIG. 6 (e.g. in step S17 in FIG. 7). Hence, in a patient 12 with a rather small concrement 18

(which can thus be missed by the shockwave more easily) and heavy breathing at the same time, with correspondingly strong deflections of the concrement 18, the averaging operation could be performed over a larger number of shockwaves and, thus, relaxation times than in another patient 12 with a rather flat breathing and a larger concrement 18 (which is thus hit more often). It is also possible to work without any averaging operation (e.g., Z=1).

It is further noted that the reference relaxation time (step S17) and the later standardization of measured relaxation times, with the help of the reference relaxation time (step S26), need not be determined so that in the variation control during shockwave therapy absolute values of the measured relaxation times are displayed on the display device 20 and evaluated accordingly. As for the lithotripter 10, which is outlined schematically in FIG. 1, it should be understood that the device 10 may comprise numerous further components, including those that are known in the art, such as an X-ray locating device or an imaging ultrasonic scanner.

While the invention has been described with respect to the foregoing exemplary embodiments, it will be apparent to those skilled in the art that various modifications, variations and improvements of the invention may be made in light of the above teachings and within the purview of the appended claims without departing from the spirit and intended scope of the invention. In regard to the foregoing description of the exemplary embodiments of the invention, areas which are known to those of ordinary skill in the art may not have been described in detail, in order to facilitate a clear and concise description of the invention. Accordingly, it should be understood that the invention is not to be limited by the specific exemplary embodiments, but only by the scope of the appended claims.

What is claimed is:

1. A hit control system for a lithotripter, the hit-control system being configured to monitor effects of a shockwave treatment to a target area inside a body of a patient, the system comprising:
   a shockwave generator that generates a shockwave for treatment of the target area;
   an ultrasonic transmitting/receiving unit comprising an ultrasonic transducer configured to emit ultrasonic pulses and to receive ultrasonic waves reflected from the target area during shockwave treatment of the target area; and
   an evaluating unit, in communication with the ultrasonic transmitting/receiving unit, that determines a correlation coefficient K of a time correlation between a first reflected ultrasonic wave and a second reflected ultrasonic wave, the reflected ultrasonic waves corresponding to successively emitted ultrasonic pulses that are reflected in the target area in which a target object is located, and the correlation being determined for a certain interval of time, wherein the evaluating unit provides a signal related to the correlation coefficient K,
   wherein at least one of
   a display device fed with the signal related to the correlation coefficient K,
   an alarm device fed with and responsive to an error signal produced by the evaluating unit and related to the coefficient K, or
   the shockwave generator, so as to stop or continue the generation of shockwaves dependent on an error signal produced by the evaluating unit and related to the coefficient K,
   is connected to the evaluating unit.

2. The system of claim 1, wherein the evaluating unit determines a temporal cross correlation function between the ultrasonic waves and to define the maximum value of the temporal cross correlation function as the correlation coefficient K.

3. The system of claim 1, wherein the ultrasonic transducer of the ultrasonic transmitting/receiving unit is mounted on an adjustable holder.

4. The system of claim 1, wherein the ultrasonic transmitting/receiving unit is a part of an imaging ultrasonic scanner.

5. The system of claim 1, wherein the ultrasonic transducer is a pin probe.

6. The system of claim 1, further comprising an X-ray locating device.

7. The system of claim 1, wherein the evaluating unit provides an error signal if, after emission of a shockwave, the minimum value of the correlation coefficient K is not less than a predetermined first threshold value.

8. The system of claim 7, wherein the evaluating unit averages the minimum value of the correlation coefficient K over a plurality of shockwaves.

9. The system of claim 7, wherein the evaluating unit standardizes the minimum value of the correlation coefficient K to a reference minimum value of a reference correlation coefficient curve.

10. The system of claim 7, further comprising means for the continuous representation of the minimum value of the correlation coefficient K over a treatment duration.

11. The system of claim 7, further comprising an alarm device in communication with the evaluating unit and supplied with the error signal.

12. The system of claim 11, wherein the alarm device outputs an optical alarm or acoustic alarm.

13. The system of claim 7, wherein the shockwave generator is in communication with the evaluating unit and stops or continues the generation of shockwaves dependent on the error signal.

14. The system of claim 7, wherein the evaluating unit comprises adjusting means for adjusting the first threshold value.

15. The system of claim 7, wherein the evaluating unit determines a temporal cross correlation function between the ultrasonic waves to define the maximum value of the temporal cross correlation function as the correlation coefficient K.

16. The system of claim 7, wherein the ultrasonic transducer of the ultrasonic transmitting/receiving unit is mounted on an adjustable holder.

17. The system of claim 7, wherein the ultrasonic transmitting/receiving unit is a part of an imaging ultrasonic scanner.

18. The system of claim 7, wherein the ultrasonic transducer is a pin probe.

19. The system of claim 7, further comprising an X-ray locating device.

20. The system of claim 1, wherein the evaluating unit provides an error signal if, after emission of a shockwave, a relaxation time ($T_R$) of the correlation coefficient K is not less than a predetermined second threshold value.

21. The system of claim 20, wherein the evaluating unit averages the relaxation time ($T_R$) of the correlation coefficient K over a plurality of shockwaves.

22. The system of claim 20, wherein the evaluating unit standardizes the relaxation time ($T_R$) of the correlation coefficient K to a reference relaxation time of a reference correlation coefficient curve.

23. The system of claim 20, further comprising means for the continuous representation of the relaxation time ($T_R$) of the correlation coefficient K over a treatment duration.

24. The system of claim 20, further comprising an alarm device in communication with the evaluating unit and supplied with the error signal.

25. The system of claim 24, wherein the alarm device outputs an optical alarm or acoustic alarm.

26. The system of claim 20, wherein the evaluating unit determines the relaxation time ($T_R$) by adapting a fit curve or a curve of the form $1-A^{(-t/T_R)}$ to the variation of the correlation coefficient K with time.

27. The system of claim 26, wherein the evaluating unit smoothes the variation of the correlation coefficient K.

28. The system of claim 20, wherein the shockwave generator is in communication with the evaluating unit and stops or continues the generation of shockwaves dependent on the error signal.

29. The system of claim 20, wherein the evaluating unit comprises adjusting means for adjusting the second threshold value.

30. The system of claim 20, wherein the evaluating unit determines a temporal cross correlation function between the ultrasonic waves to define the maximum value of the temporal cross correlation function as the correlation coefficient K.

31. The system of claim 20, wherein the ultrasonic transducer of the ultrasonic transmitting/receiving unit is mounted on an adjustable holder.

32. The system of claim 20, wherein the ultrasonic transmitting/receiving unit is a part of an imaging ultrasonic scanner.

33. The system of claim 20, wherein the ultrasonic transducer is a pin probe.

34. The system of claim 20, further comprising an X-ray locating device.

35. The system of claim 1, further comprising a display device in communication with the evaluating unit and that displays the variation of the correlation coefficient K with time.

36. The system of claim 35, wherein the evaluating unit smoothes the variation of the correlation coefficient K.

37. The system of claim 35, wherein the evaluating unit provides an error signal if, after emission of a shockwave, the minimum value of the correlation coefficient K is not less than a predetermined first threshold value.

38. The system of claim 37, wherein the evaluating unit averages the minimum value over a plurality of shockwaves.

39. The system of claim 37, wherein the evaluating unit standardizes the minimum value of the correlation coefficient K to a reference minimum value of a reference correlation coefficient curve.

40. The system of claim 37, further comprising means for the continuous representation of the minimum value of the correlation coefficient K over a treatment duration.

41. The system of claim 37, further comprising an alarm device in communication with the evaluating unit and supplied with the error signal.

42. The system of claim 41, wherein the alarm device outputs an optical alarm or acoustic alarm.

43. The system of claim 37, wherein the shockwave generator is in communication with the evaluating unit and stops or continues the generation of shockwaves dependent on the error signal.

44. The system of claim 37, wherein the evaluating unit comprises adjusting means for adjusting the first threshold value.

45. The system of claim 37, wherein the evaluating unit determines a temporal cross correlation function between the ultrasonic waves to define the maximum value of the temporal cross correlation function as the correlation coefficient K.

46. The system of claim 37, wherein the ultrasonic transducer of the ultrasonic transmitting/receiving unit is mounted on an adjustable holder.

47. The system of claim 37, wherein the ultrasonic transmitting/receiving unit is a part of an imaging ultrasonic scanner.

48. The system of claim 37, wherein the ultrasonic transducer is a pin probe.

49. The system of claim 37, further comprising an X-ray locating device.

50. The system of claim 35, wherein the evaluating unit provides an error signal if, after emission of a shockwave, a relaxation time ($T_R$) of the correlation coefficient K is not less than a predetermined second threshold value.

51. The system of claim 50, wherein the evaluating unit averages the relaxation time ($T_R$) of the correlation coefficient K over a plurality of shockwaves.

52. The system of claim 50, wherein the evaluating unit standardizes the relaxation time ($T_R$) of the correlation coefficient K to a reference relaxation time of a reference correlation coefficient curve.

53. The system of claim 50, further comprising means for the continuous representation of the relaxation time ($T_R$) of the correlation coefficient K over a treatment duration.

54. The system of claim 50, further comprising an alarm device in communication with the evaluating unit and supplied with the error signal.

55. The system of claim 54, wherein the alarm device outputs an optical alarm or acoustic alarm.

56. The system of claim 50, wherein the evaluating unit determines the relaxation time ($T_R$) by adapting a fit curve or a curve of the form $1-A^{(-t/T_R)}$ to the variation of the correlation coefficient K with time.

57. The system of claim 56, wherein the evaluating unit smoothes the variation of the correlation coefficient K.

58. The system of claim 50, wherein the shockwave generator is in communication with the evaluating unit and stops or continues the generation of shockwaves dependent on the error signal.

59. The system of claim 50, wherein the evaluating unit comprises adjusting means for adjusting the second threshold value.

60. The system of claim 50, wherein the evaluating unit determines a temporal cross correlation function between the ultrasonic waves and to define the maximum value of the temporal cross correlation function as the correlation coefficient K.

61. The system of claim 50, wherein the ultrasonic transducer of the ultrasonic transmitting/receiving unit is mounted on an adjustable holder.

62. The system of claim 50, wherein the ultrasonic transmitting/receiving unit is a part of an imaging ultrasonic scanner.

63. The system of claim 50, wherein the ultrasonic transducer is a pin probe.

64. The system of claim 50, further comprising an X-ray locating device.

65. The system of claim 1, wherein the evaluating unit determines the correlation coefficient K based on the ultrasonic waves assigned to the ultrasonic pulses directly succeeding one another.

66. The system of claim 65, wherein the evaluating unit provides an error signal if, after emission of a shockwave, the minimum value of the correlation coefficient K is not less than a predetermined first threshold value.

67. The system of claim 66, wherein the evaluating unit averages the minimum value of the correlation coefficient K over a plurality of shockwaves.

68. The system of claim 66, wherein the evaluating unit standardizes the minimum value of the correlation coefficient K to a reference minimum value of a reference correlation coefficient curve.

69. The system of claim 66, further comprising means for the continuous representation of the minimum value of the correlation coefficient K over a treatment duration.

70. The system of claim 66, further comprising an alarm device in communication with the evaluating unit and supplied with the error signal.

71. The system of claim 70, wherein the alarm device outputs an optical alarm or acoustic alarm.

72. The system of claim 66, wherein the shockwave generator is in communication with the evaluating unit and stops or continues the generation of shockwaves dependent on the error signal.

73. The system of claim 66, wherein the evaluating unit comprises adjusting means for adjusting the first threshold value.

74. The system of claim 66, wherein the evaluating unit determines a temporal cross correlation function between the ultrasonic waves and to define the maximum value of the temporal cross correlation function as the correlation coefficient K.

75. The system of claim 66, wherein the ultrasonic transducer of the ultrasonic transmitting/receiving unit is mounted on an adjustable holder.

76. The system of claim 66, wherein the ultrasonic transmitting/receiving unit is a part of an imaging ultrasonic scanner.

77. The system of claim 66, wherein the ultrasonic transducer is a pin probe.

78. The system of claim 66, further comprising an X-ray locating device.

79. The system of claim 65, wherein the evaluating unit provides an error signal if, after emission of a shockwave, a relaxation time ($T_R$) of the correlation coefficient K is not less than a predetermined second threshold value.

80. The system of claim 79, wherein the evaluating unit averages the relaxation time ($T_R$) of the correlation coefficient K over a plurality of shockwaves.

81. The system of claim 79, wherein the evaluating unit standardizes the relaxation time ($T_R$) of the correlation coefficient K to a reference relaxation time of a reference correlation coefficient curve.

82. The system of claim 79, further comprising means for the continuous representation of the relaxation time ($T_R$) of the correlation coefficient K over a treatment duration.

83. The system of claim 79, further comprising an alarm device in communication with the evaluating unit and supplied with the error signal.

84. The system of claim 83, wherein the alarm device outputs an optical alarm or acoustic alarm.

85. The system of claim 79, wherein the evaluating unit determines the relaxation time ($T_R$) by adapting a fit curve or a curve of the form $1-A^{(-t/T_R)}$ to the variation of the correlation coefficient K with time.

86. The system of claim 85, wherein the evaluating unit smoothes the variation of the correlation coefficient K.

87. The system of claim 79, wherein the shockwave generator is in communication with the evaluating unit and stops or continues the generation of shockwaves dependent on the error signal.

88. The system of claim 79, wherein the evaluating unit comprises adjusting means for adjusting the second threshold value.

89. The system of claim 79, wherein the evaluating unit determines a temporal cross correlation function between the ultrasonic waves and to define the maximum value of the temporal cross correlation function as the correlation coefficient K.

90. The system of claim 79, wherein the ultrasonic transducer of the ultrasonic transmitting/receiving unit is mounted on an adjustable holder.

91. The system of claim 79, wherein the ultrasonic transmitting/receiving unit is a part of an imaging ultrasonic scanner.

92. The system of claim 79, wherein the ultrasonic transducer is a pin probe.

93. The system of claim 79, further comprising an X-ray locating device.

94. The system of claim 75, further comprising a display device in communication with the evaluating unit and that displays the variation of the correlation coefficient K with time.

95. The system of claim 94, wherein the evaluating unit smoothes the variation of the correlation coefficient K.

96. The system of claim 94, wherein the evaluating unit provides an error signal if, after emission of a shockwave, the minimum value of the correlation coefficient K is not less than a predetermined first threshold value.

97. The system of claim 96, wherein the evaluating unit averages the minimum value of the correlation coefficient K over a plurality of shockwaves.

98. The system of claim 96, wherein the evaluating unit standardizes the minimum value of the correlation coefficient K to a reference minimum value of a reference correlation coefficient curve.

99. The system of claim 96, further comprising means for the continuous representation of the minimum value of the correlation coefficient K over a treatment duration.

100. The system of claim 96, further comprising an alarm device in communication with the evaluating unit and supplied with the error signal.

101. The system of claim 100, wherein the alarm device outputs an optical alarm or acoustic alarm.

102. The system of claim 96, wherein the shockwave generator is in communication with the evaluating unit and stops or continues the generation of shockwaves dependent on the error signal.

103. The system of claim 96, wherein the evaluating unit comprises adjusting means for adjusting the first threshold value.

104. The system of claim 96, wherein the evaluating unit determines a temporal cross correlation function between the ultrasonic waves and to define the maximum value of the temporal cross correlation function as the correlation coefficient K.

105. The system of claim 96, wherein the ultrasonic transducer of the ultrasonic transmitting/receiving unit is mounted on an adjustable holder.

106. The system of claim 96, wherein the ultrasonic transmitting/receiving unit is a part of an imaging ultrasonic scanner.

107. The system of claim 96, wherein the ultrasonic transducer is a pin probe.

108. The system of claim 96, further comprising an X-ray locating device.

109. The system of claim 94, wherein the evaluating unit provides an error signal if, after emission of a shockwave, a relaxation time ($T_R$) of the correlation coefficient K is not less than a predetermined second threshold value.

110. The system of claim 109, wherein the evaluating unit averages the relaxation time ($T_R$) of the correlation coefficient K over a plurality of shockwaves.

111. The system of claim 109, wherein the evaluating unit standardizes the relaxation time ($T_R$) of the correlation coefficient K to a reference relaxation time of a reference correlation coefficient curve.

112. The system of claim 109, further comprising means for the continuous representation of the relaxation time ($T_R$) of the correlation coefficient K over a treatment duration.

113. The system of claim 109, further comprising an alarm device in communication with the evaluating unit and supplied with the error signal.

114. The system of claim 113, wherein the alarm device outputs an optical alarm or acoustic alarm.

115. The system of claim 109, wherein the evaluating unit determines the relaxation time ($T_R$) by adapting a fit curve or a curve of the form $1-A^{(-t/T_R)}$ to the variation of the correlation coefficient K with time.

116. The system of claim 109, wherein the evaluating unit smoothes the variation of the correlation coefficient K.

117. The system of claim 109, wherein the shockwave generator is in communication with the evaluating unit and stops or continues the generation of shockwaves dependent on the error signal.

118. The system of claim 109, wherein the evaluating unit comprises adjusting means for adjusting the second threshold value.

119. The system of claim 109, wherein the evaluating unit determines a temporal cross correlation function between the ultrasonic waves and to define the maximum value of the temporal cross correlation function as the correlation coefficient K.

120. The system of claim 109, wherein the ultrasonic transducer of the ultrasonic transmitting/receiving unit is mounted on an adjustable holder.

121. The system of claim 109, wherein the ultrasonic transmitting/receiving unit is a part of an imaging ultrasonic scanner.

122. The system of claim 109, wherein the ultrasonic transducer is a pin probe.

123. The system of claim 109, further comprising an X-ray locating device.

124. A hit control method for a lithotripter, the hit-control method monitoring effects of a shockwave treatment to a target area inside a body of a patient, comprising:
  providing a shockwave generator that generates a shockwave for treatment of the target area;
  providing an ultrasonic transmitting/receiving unit comprising an ultrasonic transducer;
  providing an evaluating unit, in communication with the ultrasonic transmitting/receiving unit and the shockwave generator;
  emitting ultrasonic pulses from the ultrasonic transducer into a body during shockwave treatment of the target area;
  receiving ultrasonic waves reflected from a target area in the body in which a target object is located via the transducer;
  evaluating the received ultrasonic waves via the evaluating unit to determine a correlation coefficient K of a time correlation between a first reflected ultrasonic wave and a second reflected ultrasonic wave, the reflected ultrasonic waves corresponding to successively emitted ultrasonic pulses that are reflected in the target area in which a target object is located, and the correlation being determined for a certain interval of time, and
  providing a signal related to the correlation coefficient K from the evaluating unit,
  providing at least one of
  a display device in connection with the evaluating unit and fed with the signal related to the correlation coefficient K,
  an alarm device in connection with the evaluating unit, feeding it with and responsive to an error signal produced by the evaluating unit and related to the correlation coefficient K, or
  the shockwave generator in communication with the evaluating unit and stopping or continuing the generation of shockwaves dependent on an error signal produced by the evaluating unit and related to the correlation coefficient K.

125. The method of claim 124, wherein evaluating the received ultrasonic waves comprises determining the correlation coefficient K based on the ultrasonic waves assigned to the ultrasonic pulses directly succeeding one another.

126. The method of claim 124, wherein evaluating the received ultrasonic waves comprises determining a temporal cross correlation function between the ultrasonic waves and defining the maximum value of the temporal cross correlation function as the correlation coefficient K.

127. The method of claim 124, further comprising continuously representing the minimum value of the correlation coefficient K during a shockwave treatment of the body.

128. The method of claim 124, further comprising continuously representing the relaxation time ($T_R$) of the correlation coefficient K during a shockwave treatment of the body.

129. The method of claim 124, further comprising:
  providing a display device in communication with the evaluating unit;
  positioning the body within a focus of the shockwave generator;
  displaying the target object and the focus on the display device;
  adjusting the position of the body to place the target object within the focus of the shockwave generator;
  determining the minimum value of the correlation coefficient K after the emission of a shockwave from the shockwave generator; and
  storing the minimum value as a reference minimum value.

130. The method of claim 129, further comprising standardizing the minimum value of a second correlation coefficient (K'), measured at a later time, to the reference minimum value.

131. The method of claim 129, further comprising continuously representing the minimum value of the correlation coefficient K during a shockwave treatment of the body.

132. The method of claim 124, further comprising:
  providing a display device in communication with the evaluating unit;
  positioning the body within a focus of the shockwave generator;
  displaying the target object and the focus on the display device;
  adjusting the position of the body to place the target object within the focus of the shockwave generator;
  determining the relaxation time ($T_R$) of the correlation coefficient K after the emission of a shockwave from the shockwave generator; and
  storing the relaxation time ($T_R$) as reference relaxation time.

133. The method of claim 132, further comprising standardizing the relaxation time ($T_R$) of a second correlation coefficient (K'), measured at a later time, to the reference relaxation time.

134. The method of claim 132, further comprising continuously representing the relaxation time ($T_R$) of the correlation coefficient K during a shockwave treatment of the body.

135. The method of claim 124, further comprising providing an error signal from the evaluating unit to the shockwave generator if, after emission of a shockwave, the minimum value of the correlation coefficient K is not less than a predetermined first threshold value.

136. The method of claim 135, further comprising averaging the minimum value of the correlation coefficient K over a plurality of shockwaves.

137. The method of claim 135, further comprising standardizing the minimum value of the correlation coefficient K to a reference minimum value of a reference correlation coefficient curve.

138. The method of claim 124, further comprising providing an error signal from the evaluating unit to the shockwave generator if, after emission of a shockwave, the relaxation time ($T_R$) of the correlation coefficient K is not less than a predetermined second threshold value.

139. The method of claim 138, further comprising averaging the relaxation time ($T_R$) of the correlation coefficient K over a plurality of shockwaves.

140. The method of claim 138, further comprising standardizing the relaxation time ($T_R$) of the correlation coefficient K to a reference relaxation time of a reference correlation coefficient curve.

141. The method of claim 124, wherein the treatment is a lithotripsy treatment.

142. The method of claim 141, wherein the treatment is the fragmentation of a target object in said target area.

143. The method of claim 124, wherein the correlation coefficient $K_{i,k}$ of a time correlation between the first reflected ultrasonic wave $e_i(t)$ and the second reflected ultrasonic wave $e_{i+k}(t)$ is determined by $$\int_{T_1}^{T_2} e_i(t) * e_{i+k}(t) \, dt,$$

wherein the interval of time is determined by the points in time $T_1$ and $T_2$.

144. The method of claim 143, wherein the correlation coefficient $K_{i,k}$ is standardized by means of the factor $$\left(\int_{T_1}^{T_2} e_i^2(t) dt\right)^{\frac{1}{2}} \left(\int_{T_1}^{T_2} e_{i+k}^2(t) dt\right)^{\frac{1}{2}}.$$

145. The system of claim 1, wherein the correlation coefficient $K_{i,k}$ of a time correlation between the first reflected ultrasonic wave $e_i(t)$ and the second reflected ultrasonic wave $e_{i+k}(t)$ is determined by $$\int_{T_1}^{T_2} e_i(t) * e_{i+k}(t) \, dt,$$

wherein the interval of time is determined by the points in time $T_1$ and $T_2$.

146. The system of claim 145, wherein the correlation coefficient $K_{i,k}$ is standardized by means of the factor $$\left(\int_{T_1}^{T_2} e_i^2(t) dt\right)^{\frac{1}{2}} \left(\int_{T_1}^{T_2} e_{i+k}^2(t) dt\right)^{\frac{1}{2}}.$$

147. The system of claim 1, wherein the treatment is a lithotripsy treatment.

148. The system of claim 147, wherein the treatment is the fragmentation of a target object in said target area.

* * * * *